(12) United States Patent
Parker et al.

(10) Patent No.: US 8,999,378 B2
(45) Date of Patent: Apr. 7, 2015

(54) POROUS ELECTROACTIVE HYDROGELS AND USES THEREOF

(75) Inventors: Kevin Kit Parker, Waltham, MA (US); Megan O'Grady, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 767 days.

(21) Appl. No.: 13/120,003

(22) PCT Filed: Sep. 24, 2009

(86) PCT No.: PCT/US2009/058219
§ 371 (c)(1),
(2), (4) Date: Jun. 2, 2011

(87) PCT Pub. No.: WO2010/036800
PCT Pub. Date: Apr. 1, 2010

(65) Prior Publication Data
US 2012/0029416 A1  Feb. 2, 2012

Related U.S. Application Data

(60) Provisional application No. 61/194,079, filed on Sep. 24, 2008, provisional application No. 61/200,609, filed on Dec. 2, 2008.

(51) Int. Cl.
| | | |
|---|---|---|
| *A61N 1/30* | (2006.01) | |
| *C12N 5/071* | (2010.01) | |
| *B01L 3/00* | (2006.01) | |
| *A61K 47/30* | (2006.01) | |
| *A61P 9/00* | (2006.01) | |
| *B01J 39/20* | (2006.01) | |
| *A61K 35/12* | (2006.01) | |
| *C12Q 1/02* | (2006.01) | |
| *A61F 13/02* | (2006.01) | |
| *A61F 13/06* | (2006.01) | |
| *A61F 13/10* | (2006.01) | |

(52) U.S. Cl.
CPC ............... *A61F 13/02* (2013.01); *A61F 13/06* (2013.01); *A61F 13/10* (2013.01)

(58) Field of Classification Search
None
See application file for complete search history.

(56) References Cited

U.S. PATENT DOCUMENTS

| | | | | |
|---|---|---|---|---|
| 2003/0083389 A1* | 5/2003 | Kao et al. | ........................ | 516/98 |
| 2004/0182704 A1* | 9/2004 | Daunert et al. | ............... | 204/405 |

OTHER PUBLICATIONS

O'Grady et al., "Optimization of Electroactive Hydrogel Actuators", ACS Applied Materials and Interfaces, 2:343-346 (2009).
Baughman, "Playing Nature's Game with Artificial Muscles", Science, 308, 63-65 (005).
Madden et al., "Artificial Muscle Technology: Physical Principles and Naval Prospects", IEEE J. Oceanic Eng., 29, 706-728 (2004).
Onoda et al., "Artificial Muscle Using Conducting Polymers", Electr. Eng. Jpn., 149, 7-13 (2004).
Moschou et al., "Artificial Muscle Material with Fast Electroactuation under Neutral pH Conditions", Chem. Mater. 16, 2499-2502 (2004).
Moschou et al., "Voltage-switchable artificial muscles actuating at near neutral pH", Sensor Actuat. B-Chemical 115, 379-383 (2006).
Otero et al., "Polypyrrole artificial muscles: a new rhombic element. Construction and electrochemomechanical characterization", Appl. Electrochem., 36, 205-214 (2006).
Takashima et al., "Patternable bi-ionic actuator: an example of new functionality of actuation, folding and unfolding of electrochemical spring", Sensor Actuat. B-Chemical, 110, 120-124 (2005).
Bay et al., "A Conducting Polymer Artificial Muscle with 12% Linear Strain", Adv. Mater., 15, 310-313 (2003).
Jager et al., "Microfabricating Conjugated Polymer Actuators", Science, 290, 1540-1545 (2000).
Shiga et al., "Deformation and Viscoelastic Behavior of Polymer Gels in Electric Fields", Adv. Polym. Sci. 134, 131-163 (1997).
Grimshaw et al., "Kinetics of electrically and chemically induced swelling in polyelectrolyte Gels", J. Chem. Phys., 93, 4462-4472 (1990).
Yao et al., "Electromechanical Responses of Strong Acid Polymer Gels in DC Electric Fields", Macromolecules 36, 2055-2065 (2003).
Doi et al., "Deformation of Ionic Polymer Gels by Electric Fields", Macromolecules 25, 5504-5511 (1992).
Tokuyama et al., "Novel Synthesis of Macroporous Poly(N-isopropylacrylamide) Hydrogels Using Oil-in-Water Emulsions", Langmuir, 23, 11246-11251 (2007).
Mason et al. "Elasticity of Compressed Emulsions", Phys. Rev. Lett. 75, 2051-2054 (1995).
Wallmersperger et al., "Coupled chemo-electro-mechanical formulation for ionic polymer gels—numerical and experimental investigations", Mech. Mater. 36, 411-420 (2004).
Yew et al., "Analysis of pH and electrically controlled swelling of hydrogel-based micro-sensors/actuators", Biomed. Microdevices 9, 487-499 (2007).
Koneshan, et al., "Solvent Structure, Dynamics, and Ion Mobility in Aqueous Solutions at 25° C.", S. Phys. Chem. B 102, 4193-4204 (1998).

* cited by examiner

*Primary Examiner* — Robert A Wax
*Assistant Examiner* — Danah Al-Awadi
(74) *Attorney, Agent, or Firm* — McCarter & English; Maria Laccotripe Zacharakis; Deborah L. Nagle

(57) ABSTRACT

The present invention provides porous electroactive hydrogels, the deformation angle of which is controlled by electroactuation, and methods for preparing and using such hydrogels.

27 Claims, 11 Drawing Sheets

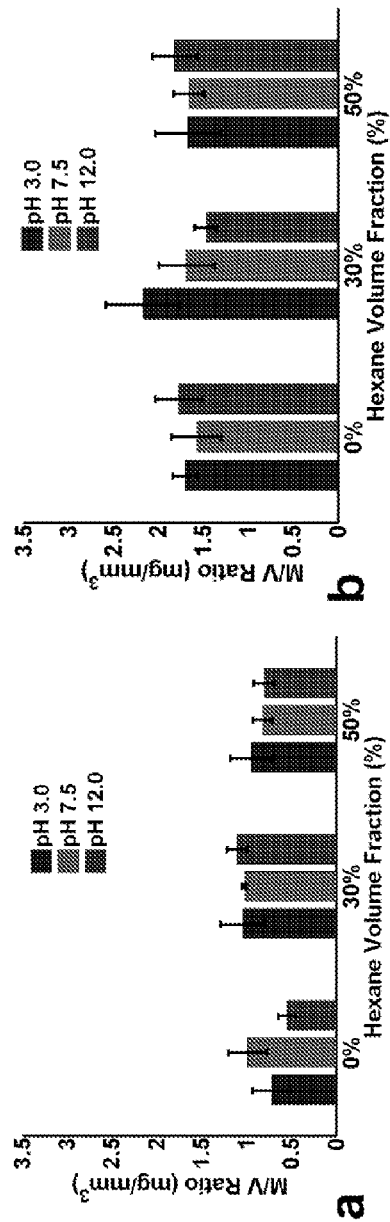
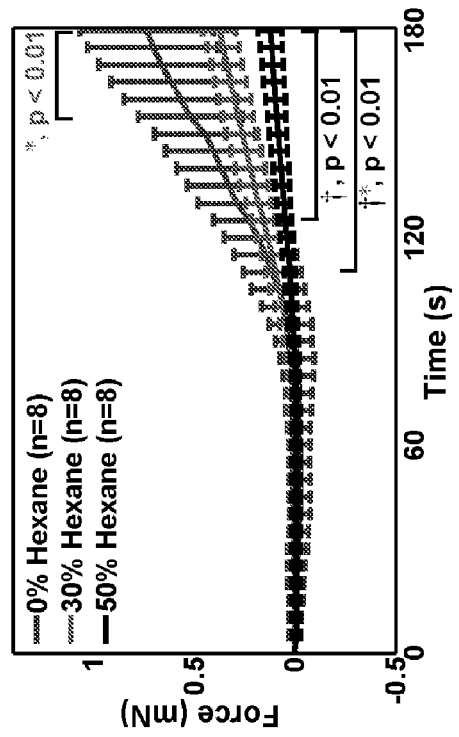
Figure 14
Figure 15

US 8,999,378 B2

POROUS ELECTROACTIVE HYDROGELS AND USES THEREOF

RELATED APPLICATIONS

This application claims the benefit of and priority to U.S. Provisional Patent Application Ser. No. 61/194,079, filed on Sep. 24, 2008, and U.S. Provisional Application Ser. No. 61/200,609, filed on Dec. 2, 2008. The entire contents of each of the foregoing provisional applications are incorporated herein by reference.

GOVERNMENT SUPPORT

This invention was made with U.S. government support under grant nos. PHY-0117795 and DMR-0213805 awarded by the National Science Foundation and FA9550-05-1-0459 awarded by the U.S. Air Force Office of Scientific Research, Defense Advanced Research Projects Agency (DARPA) Bio-SenSE Program. The U.S. Government has certain rights in the invention.

BACKGROUND OF THE INVENTION

Hydrogels are hydrophilic polymer networks produced from reactions of one or more monomers or by association bonds between chains that can absorb from at least 20% to up to thousands of times their dry weight in water. Hydrogels may be chemically stable or they may disintegrate and dissolve with time. Hydrogels may be classified as either physical or chemical. Physical hydrogels have networks held together by molecular entanglements and/or secondary forces such as hydrogen bonding, van der Waals interactions, ionic or hydrophobic forces. Physical hydrogels are not homogeneous due to regions of high crosslinking density and low water swelling, called clusters, dispersed within low crosslinking density and high water swelling, or hydrophobic or ionic domains that create inhomogeneities. Chemical hydrogels are covalently crosslinked networks and may be generated by the crosslinking of water-soluble polymers, or by converting hydrophobic polymers to hydrophilic polymers. Chemical hydrogels are also not homogeneous due to clusters of molecular entanglements. Chain loops and free chain ends also produce network defects in both physical and chemical hydrogels, and they do not contribute to the permanent network elasticity.

Electroactive hydrogels are those hydrogels prepared using a polyelectrolyte polymer and whose shape and/or dimensions are altered upon pH and/or modest electric field change. For example, in a charged polyelectrolyte polymer, the polymer chains are chemically linked to one another through cross linking sites and swollen by solvent molecules, such as water that "ionize" the acid or salt groups along the polymer backbone to yield mobile hydrated ions (e.g., cations) and immobile anions attached to the polymer backbone. It is the mobility of hydrated ions, afforded by swelling the hydrogel with a suitable solvent, that leads to an electroactive response.

Common applications for hydrogels include use in superabsorbant materials, contact lenses and cosmetics. In addition, hydrogel materials have been used for drug delivery and to replace or reconstruct soft tissues. However, the utility of such hydrogels has been hindered due to limitations in the elasticity, force generation abilities and responsiveness of the prior art hydrogels.

Accordingly, there is a need in the art for improved electroactive hydrogels and methods of making such hydrogels.

SUMMARY OF THE INVENTION

The present invention provides a solution to earlier limitations of electroactive hydrogels. The present invention provides electroactive polymer hydrogels which, among other things, contract fast and are able to bend more easily and to a larger extent as compared to the prior art hydrogels. The electroactive polymer hydrogels of the present invention have been engineered to maximize electroactuation by incorporating porous scaffolds in the hydrogels. Without intending to be limited by theory, it is believed that the porosity in the hydrogels of the present invention decreases the cross-sectional area of the hydrogel, such that the hydrogel requires less COOH groups on the anode side of the hydrogel to produce a bending motion. In addition, the porosity decreases the Young's modulus of the hydrogels and enhances the deswelling and mechanical properties to further improve the actuation of these hydrogels. The improved electroactive hydrogels provided herein are durable, responsive, and suitable for use in a clinical setting, e.g., suitable for use as artificial muscle constructs, as well as for use in non-clinical applications such as use as soft robotic manipulators.

Accordingly, in one aspect the present invention provides porous electroactive hydrogels which bend at an angle greater than about 30 degrees, greater than about 35 degrees, greater than about 40 degrees, greater than about 45 degrees, greater than about 50 degrees, greater than about 55 degrees, greater than about 60 degrees, greater than about 65 degrees, greater than about 70 degrees, greater than about 75 degrees, greater than about 80 degrees, greater than about 85 degrees, greater than about 90 degrees, greater than about 95 degrees, or greater than about 100 degrees upon electroactuation by an electric field as compared to the bending of the hydrogel in the absence of the electric field. In one embodiment, the electric field is about 0.1 Volts/cm, about 0.25 Volts/cm, about 0.5 Volts/cm, about 1 Volts/cm, about 1.5 Volts/cm, about 2 Volts/cm, about 2.5 Volts/cm, about 3 Volts/cm, about 3.5 Volts/cm, about 4 Volts/cm, about 4.5 Volts/cm, about 5 Volts/cm, about 5.5 Volts/cm, or about 6 Volts/cm. In one embodiment, the electric field is applied to the hydrogel for about 15 seconds, for about 30 seconds, for about 45 seconds, for about 1 minute, for about 1.25 minutes, for about 1.5 minutes, for about 1.75 minutes, for about 2 minutes, for about 2.25 minutes, for about 2.5 minutes, for about 2.75 minutes, for about 3 minutes, for about 3.25 minutes, for about 3.5 minutes, for about 3.75 minutes, for about 4 minutes, for about 4.25 minutes, for about 4.5 minutes, for about 4.75 minutes, or for about 5 minutes. In one embodiment, the hydrogel comprises pores having a radius of about 0.5 micrometers ($\mu m$), about 1 $\mu m$ about 1.5 $\mu m$ about 2 $\mu m$ about 2.5 $\mu m$ about 3 $\mu m$ about 3.5 $\mu m$ about 4 $\mu m$ about 4.5 $\mu m$ about 5 $\mu m$ about 5.5 $\mu m$ about 6 $\mu m$ about 6.5 $\mu m$ about 7 $\mu m$, about 7.5 $\mu m$, about 8 $\mu m$, about 8.5 $\mu m$, about 9 $\mu m$, about 9.5 $\mu m$, or about 10 $\mu m$. In another embodiment, the hydrogel comprises an anisotropic pattern. In other embodiments of the invention, the hydrogel further comprises an electrode, a voltage source, a pharmaceutically active compound, a chromatophore, or a cell, such as a myocyte, e.g., a cardiac myocyte or a skeletal myocyte. In another embodiment, the hydrogels of the invention do not comprise a cell.

In another aspect, the present invention provides methods for preparing porous electroactive hydrogels. In one embodiment, the methods include contacting a pre-polymer solution of a polyelectrolyte hydrogel with a water insoluble solution and a surfactant, thereby generating a polymer emulsion, wherein the polymer emulsion comprises about 40%, about 45%, about 50%, about 55%, about 60%, about 65%, about 70%, about 75%, or about 80% by volume of the pre-polymer solution and about 20%, about 25%, about 30%, about 35%, about 40%, about 45%, about 50%, about 55%, or about 60% by volume of the water insoluble solution; contacting the polymer emulsion with an oxidizing agent, thereby generating a porous electroactive hydrogel and a disperse water insoluble solution; and removing the disperse water insoluble solution, thereby preparing a porous electroactive hydrogel. In another embodiment, the methods include placing a pre-polymer solution in a mold comprising polymeric fibers; contacting the pre-polymer solution with an oxidizing agent, thereby generating an electroactive hydrogel and a disperse water insoluble solution; dissolving the polymeric fibers; and removing the disperse water insoluble solution, thereby preparing a porous electroactive hydrogel.

The methods of the invention may further comprise, placing a photolithographic mask on top of the polymer emulsion, placing the polymer emulsion in a mold which may comprise a pattern such as a pattern comprising grooves of dimensions of about 1 millimeter by about 1 millimeter by about 5 millimeter, about 0.5 millimeter by about 0.5 millimeter by about 2.5 millimeter, about 0.1 millimeter by about 0.1 millimeter by about 0.5 millimeter, about 1.5 millimeter by about 1.5 millimeter by about 5 millimeter, or about 2 millimeter by about 2 millimeter by about 5 millimeter. The methods of the invention may also further comprise seeding a cell, such as a skeletal muscle cell, a smooth muscle cell, or a cardiac muscle cell, on the porous electroactive hydrogel and culturing the cells, adding a chromatophore to the hydrogel, or adding a protein to the hydrogel, such as a pro-apoptotic protein. In one embodiment, the methods of the invention do not comprise seeding a cell on the hydrogel.

In one embodiment, the pre-polymer solution comprises a negatively-charged monomer, such as acrylic acid or a derivative thereof, a cross-linking agent, an acid dopant, and/or a light-sensitive oxidizer.

The present invention also provides the porous electroactive hydrogels prepared according to the methods of the invention.

In another aspect, the invention provides a polymeric ventricular assist device comprising a porous electroactive hydrogel, an extracellular matrix protein (ECM), and a cardiomyocyte linked to the ECM.

In yet another aspect, the present invention provides methods of augmenting myocardial function. The methods include contacting myocardial tissue with a porous electroactive hydrogel, applying an electrical field to the hydrogel, and systematically toggling a magnitude or polarity of an applied voltage, thereby augmenting myocardial function.

In yet another aspect, the present invention provides a biohybrid prosthetic device which includes a support structure comprising an articulating joint, such as an arm or leg, and a porous electroactive hydrogel affixed thereto.

In another aspect, the invention provides a microfluidic device, comprising a lumen and a porous electroactive hydrogel disposed within the lumen.

In yet another aspect, the invention provides an anti-biofouling device comprising a porous electroactive hydrogel.

In another aspect, the invention provides a biosensor device comprising a porous electroactive hydrogel.

Other features and advantages of the invention will be apparent from the following detailed description and claims.

BRIEF DESCRIPTION OF THE DRAWINGS

FIGS. 1C and 1D are scanning electron microscopy (SEM) images of porous PAANa hydrogels (c, d). The SEM images indicated large pores (>10 µm) using 30% (c) and 50% (d) hexane volume fractions with 0.15 M Tween 20 surfactant.

FIGS. 5A and 5D are graphs depicting the trajectory of hydrogels polymerized using 0%, 30% and 50% hexane in 2.5 V/cm (a) and 1.5 V/cm (d) electric fields.

FIGS. 5B, 5C, 5E, and 5-F are a series of photographs showing that PAANa hydrogels polymerized using 0%, 30% and 50% hexane in 2.5 V/cm (a) and 1.5 V/cm (d) electric fields 'swim' along a desired trajectory by changing the polarity of the applied voltage at various timepoints. When 2.5 V/cm is applied to the in the saline solution, the porous hydrogel initially bends toward the cathode the same extent as the non-porous hydrogel, but bends towards the anode after ~100 s. At 180 s, a significant pH gradient has been generated across the hydrogel (b,c). When 1.5 V/cm is applied, the hydrogel bends towards the cathode and no marked pH gradient is present across the hydrogel surface (e,f). These results suggest the spatiotemporal formation of a pH gradient across the hydrogel mediates the PAANa bending angle. Error bars represent the standard error of the mean of the measurements. Scale bar=2 mm.

FIGS. 14A-14B are graphs showing the measurement of the volume density of the PAANa hydrogels before hydration (a) and after placement in pH 3.0, 7.5 and 12.0 solutions for 24 hours (b). Although the mass per unit volume of the gels increase when hydrated, no significant differences were observed between porous and non-porous hydrogels. These results indicate that the water content between the porous and non-porous hydrogels is equivalent and the water content does not vary as a function of pH once hydrated (b). For each pH condition, n=12 and n=4 for each volume fraction condition (0%, 30% or 50% hexane).

FIG. 15 is a graph showing that the force generated by porous hydrogels was significantly less than non-porous hydrogels with 2.5 V/cm applied. In particular, for the hydrogels produced in 30% and 50% emulsions, the force generated was less than non-porous hydrogels after 155 s and 125 seconds, respectively (p<0.01). After 110 seconds, the force generated by the PAANa gels produced in a 50% emulsion was less than the gels produced in a 30% emulsion (p<0.01). After 180 s, the maximum force generated was 0.74+0.33 mN (s.d., n=8) for non-porous hydrogels, as compared to 0.37+0.12 mN (s.d., n=8) for gels created in a 30% emulsion and 0.12+0.06 mN (s.d., n=8) for gels created in a 30% emulsion and 0.12+0.06 mN.

DETAILED DESCRIPTION OF THE INVENTION

Figure 1B:
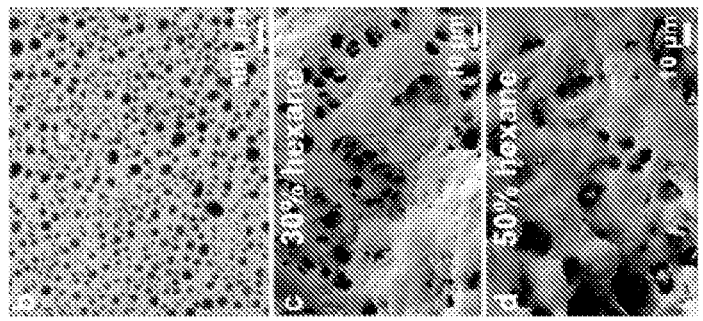
FIG. 1B is a photograph of hexane droplets spreading on the pre-polymerization solution displaying a polydisperse distribution of pore sizes (b), although the pore size varied with time in solution and shear stress applied.

The present invention provides porous electroactive hydrogels, as well as methods for generating and using the same. The various aspects of the invention are described in the sub-sections below.

I. Porous Electroactive Hydrogels

Electroactive polymer hydrogels, e.g., polymer hydrogels whose shape is modified when a voltage is applied to them, are promising materials for biological applications, because they can operate in physiological solutions at near neutral pH, require low voltages for actuation (e.g., about 1 to about 5 V), are biocompatible, flexible, and are easily fabricated. Although hydrogels and conductive polymers have been utilized for artificial muscle applications, previous electroactive polymer constructs were not engineered to maximize electroactuation by incorporating porous scaffolds in the hydrogels and/or were not engineered to mimic structural and functional aspects of biological tissue in vivo.

As described in the appended examples, a hierarchical biomimetic design was implemented to significantly enhance the degree of bending or deformation of electroactuated hydrogels. In order to decrease $Na^+$ diffusion time, an emulsion polymerization was utilized to create porous hydrogels. These porous electroactive hydrogels display increased bending angles and faster electroactuation than those reported in the literature (see, e.g., Moschou et al., (Sensors and Actuators B 2006, vol. 115, pp. 379-383), demonstrating the importance of optimizing $Na^+$ diffusion to increase hydrogel contraction. For example, unlike earlier hydrogels, the porous electroactive hydrogels described herein bend to an angle of greater than about 35 degrees.

As used herein, the term "electroactive" as it applies to polymer hydrogels of the present invention, refers to a hydrogel whose physical properties, e.g., shape, are modified when a voltage is applied to it.

As used herein, the term "electroactuation" refers to the generation of a pH gradient across a hydrogel as the result of placing the hydrogel in an electric field.

In one aspect, the present invention provides a porous electroactive hydrogel, e.g., a planar porous electroactive hydrogel, that bends at an angle greater than about 30 degrees upon electroactuation by an electrical field as compared to the bending of the hydrogel in the absence of said electric field. In other embodiments, the porous electroactive hydrogels of the invention bend at an angle greater than about 30 degrees, greater than about 35 degrees, greater than about 40 degrees, greater than about 45 degrees, greater than about 50 degrees, greater than about 55 degrees, greater than about 60 degrees, greater than about 65 degree, greater than about 70 degrees, greater than about 75 degrees, greater than about 80 degrees, greater than about 85 degrees, greater than about 90 degrees, greater than about 95 degrees, or greater than about 100 degrees when electroactuated by an electric field as compared to the bending of the hydrogel in the absence of the electric field. In one embodiment, a hydrogel of the invention bends to an angle of greater than 90 degrees within about 1 minute, about 1.5 minutes, about 2 minutes, about 2.5 minutes, about 3 minutes, about 3.5 minutes, or about 4 minutes following application of an electrical field. In one embodiment, the electric field is applied to the hydrogel for about 15 seconds, for about 30 seconds, for about 45 seconds, for about 1 minute, for about 1.25 minutes, for about 1.5 minutes, for about 1.75 minutes, for about 2 minutes, for about 2.25 minutes, for about 2.5 minutes, for about 2.75 minutes, for about 3 minutes, for about 3.25 minutes, for about 3.5 minutes, for about 3.75 minutes, for about 4 minutes, for about 4.25 minutes, for about 4.5 minutes, for about 4.75 minutes, or for about 5 minutes. It should be understood that angles and times intermediate to the above-recited angles and times are also contemplated by the present invention.

The bending of the hydrogels occurs under physiological conditions and in response to an electric field in the range of, for example, about 1 to about 5 volts/cm. Without wishing to be bound by theory, it is believed that the superior responsiveness of the porous electroactive hydrogels of the present invention originates from optimization of ion diffusion to generate the required force for bending. The rate of ion diffusion is dependent upon the pore size and/or anisotropic pattern fabricated into or onto the hydrogel construct.

In one embodiment, the electric field applied to the porous electroactive hydrogel is about 0.5 Volts/centimeter (V/cm), about 1 Volt/cm, about 1.5 Volts/cm, about 2 Volts/cm, about 2.5 Volts/cm, about 3 Volts/cm, about 3.5 Volts/cm, about 4 Volts/cm, about 4.5 Volts/cm, about 5 Volts/cm, about 5.5 Volts/cm, or about 6 Volts/cm. It should be understood that electric fields intermediate to the above-recited electric fields are also contemplated by the present invention.

The porous electroactive hydrogels of the present invention comprise pores having a radius of about 0.5 micrometers (μm), about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm. It should be understood that radii intermediate to the above-recited radii are also contemplated by the present invention.

In other embodiments, the porous electroactive hydrogels comprise an anisotropic pattern, e.g., a pattern whose properties (e.g., electrical conductivity and/or elasticity) are dependent on the direction in which the properties are measured.

As described in more detail below, other embodiments of the invention include porous electroactive hydrogels further comprising, for example, cells, an electrode, a voltage source, florescent beads, a pharmaceutically active compound, a protein, e.g., a pro-apoptotic protein or an extracellular matrix protein, and/or chromatophores. In one embodiment of the invention, the porous electroactive hydrogels do not comprise cells.

II. Methods for Preparing Electroactive Hydrogels

As described in the examples below, the improved porous electroactive hydrogels described herein may be prepared using an emulsion templating technique which overcomes the limitations of earlier processes (Moschou et al., Sensors and Actuators B 115 (2006) 379-383; Moschou et al., Chemistry of Materials 16 (2004) 2499-2502). For example, the fabrication method described herein utilizes emulsion polymerization to decrease diffusion time of ions, which leads to superior performance of the resulting porous electroactive hydrogels. Patterning and molding of the hydrogel construct may further improve electroactuation and contractile/bending performance. In addition to improved ion diffusion time, porous electroactive hydrogels made using the emulsion polymerization methods described herein are preferred for, e.g., production of artificial muscle constructs due to strength and durability requirements for such applications.

Figure 1A:
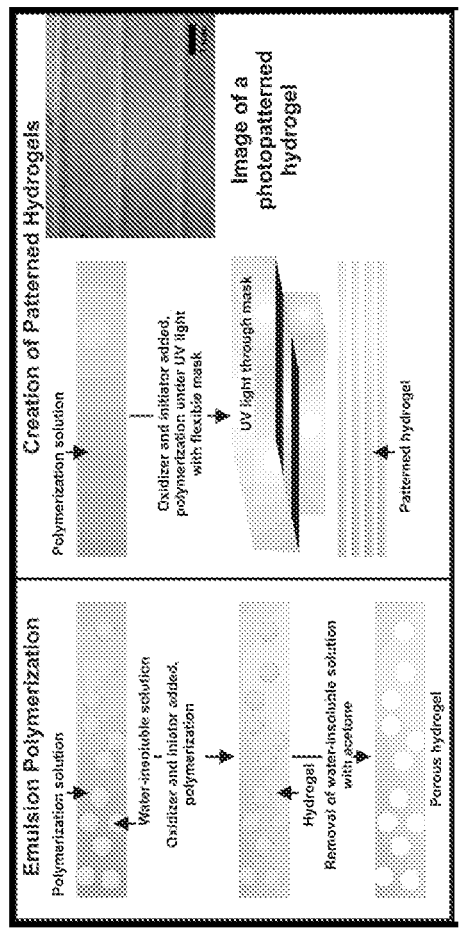
FIG. 1A is a diagram showing steps included in the methods disclosed herein for preparing porous (left) and patterned porous (right) electroactive hydrogels. Patterning a porous electroactive hydrogel may be accomplished by exposure to electromagnetic readioation, e.g., ultraviolet light, and/or by polymerizing the polymers in a mold comprising desired dimensions. Patterns that maximize diffusion to the center of the hydrogel (e.g., circles in the hydrogel center) may increase contraction, and the emulsion polymerization of the polymer may have a marked effect on the electroactuation properties of the hydrogel.

The methods of the invention generally include free radical polymerization of a polyelectrolyte hydrogel monomer in an emulsion, e.g., an oil-in-water (O/W) emulsion. The emulsion is formed by producing, e.g., oil droplets in an aqueous pre-polymerization solution and utilizing surfactants to stabilize the surface tension at the oil/water interface. The hydrogel is then polymerized using free radical polymerization, and the disperse oil phase is removed by washing with an appropriate solvent. An exemplary method for generating a porous electroactive hydrogel is depicted in FIG. 1.

In various embodiments of the invention, the methods for producing a porous electroactive hydrogel may include the steps of contacting a pre-polymer solution of a polyelectrolyte hydrogel with a water insoluble solution and a surfactant, thereby generating a polymer emulsion, contacting the polymer emulsion with an oxidizing agent and removing the disperse water insoluble solution. The emulsion may comprise about 40%, about 45%, about 50%, about 55%, about 60%, about 65%, about 70%, about 75%, or about 80% by volume of the pre-polymer solution and about 20%, about 25%, about 30%, about 35%, about 40%, about 45%, about 50%, about 55%, or about 60% by volume of the water insoluble solution. It should be understood that amounts intermediate to the above-recited amounts are also contemplated by the present invention.

The pre-polymer solution may be prepared by forming an alkaline solution of monomer, acid dopants, and an oxidizer and heating the solution past the glass transition temperature of the oxidizer. A crosslinker is added to the heated pre-polymer solution in the desired concentration. The surfactant may be added to the water insoluble aqueous solution or the monomer solution.

The pre-polymer solution is contacted with the water-insoluble solution in the desired volume fraction and mixed such that an emulsion is formed. A catalyst may added to the emulsion solution and the emulsion is subsequently exposed to an oxidizing agent to initiate polymerization.

Following polymerization, the polymer may be placed in an agent to remove the dispersed phase of the emulsion, e.g., placed in acetone or methanol. Subsequently, the hydrogel may either be dried or pre-conditioned for use.

Suitable monomers from which the porous electroactive hydrogels of the invention may be prepared include any polyelectrolyte hydrogel monomer which is polymerized using free-radical polymerization. In certain embodiments of the invention, the monomer comprises negatively-charged side chains, e.g., COO⁻ or COOH, e.g., a monomer comprising an acrylate group, e.g., poly(ethylene glycol) diacrylate, acrylic acid, polyacrylamide.acrylic acid, hydroxyethyl methacrylate, and derivatives thereof. In one embodiment, the monomer is poly(sodium acrylate). In another embodiment, the monomer comprises polyvinyl alcohol. In other embodiments of the invention, suitable monomers may comprise mixtures of monomers, e.g., poly(sodium acrylate) and polyethylene oxide or polyethylene glycol. Such mixtures of polymers are useful in inhibition and/or prevention of biofouling, discussed in more detail below.

In order to cross-link the monomers, a cross-linking agent is included. Non-limiting exemplary crosslinkers include bisacrylamide, poly(ethylene glycol) diacrylate, derivatives and combinations thereof.

Acid dopants may be incorporated into the pre-emulsion solution to facilitate electrostatic repulsion within the polymer milieu. Suitable acid dopants include maleic acid, maleic anhydride, and glutonic acid. An alkaline solution such as NaOH may be used to make negatively charged groups on the monomer and acid dopants become weak electrolytes.

To form the emulsion and subsequently the pores in the polymerized hydrogel, a water insoluble aqueous solution may be used to form the dispersed phase in the emulsion using water as the dominant phase. Suitable non-limiting examples of a water insoluble aqueous solution include hexane, oleyl alcohol or polydimethylsiloxane (PDMS).

A surfactant may be used to stabilize the emulsion by stabilizing the interface between water and the water insoluble solvent. Exemplary surfactants include Tween 20, Tween 80, sodium dodecyl sulphate, and dodecylbenzene sulfonate.

A chemical oxidizer such as ammonium persulfate or potassium persulfate may be used to allow monomer and cross-linker to bind via free-radical polymerization (oxidation of monomer and cross-linker). In certain embodiments of the invention, a light-sensitive oxidizer is used. UV light is required when using a light-sensitive oxidizer. Light-sensitive oxidizers such as Ingracure™ may be used to allow monomer and cross-linker to bind via free-radical polymerization (oxidation of monomer and cross-linker) when a UV light is exposed to the polymer solution. A catalyst such as N,N,N',N'-Tetramethylethylenediamine (TEMED) may be used to speed up oxidation reaction during polymerization.

A suitable pre-conditioning solution in which the porous electroactive hydrogel may be placed preferably has a pH of about 7 to about 7.6. In certain embodiments, the pre-conditioning solution comprises a NaCl concentration that is higher than the concentration of other components in the buffer. In one embodiment, a suitable re-conditioning solution is Tyrode's solution: 135 mmol/L NaCl, 5.4 mmol/L KCl, 1.8 mmol/L $CaCl_2$, 1 mmol/L $MgCl_2$, 0.33 mmol/L $NaH_2PO_4$, 5 mmol/L HEPES (4-(2-hydroxyethyl)-1-piperazineethanesulfonic acid), and 5 mmol/L glucose.

Figure 10A:
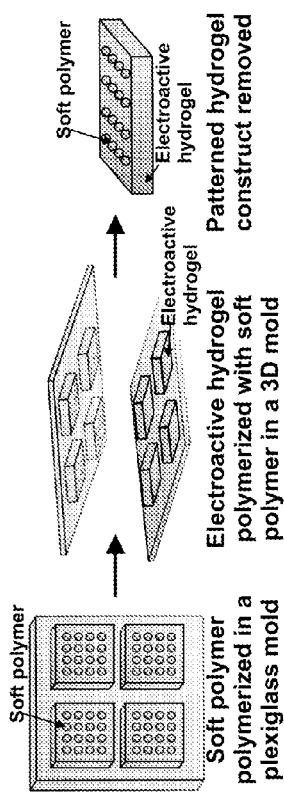
FIGS. 10A and 10B depict methods for patterning of soft polymer/electroactive hydrogel constructs. As evidenced therein, mechanical forces in patterned soft polymer and electroactive hydrogel can be modulated by toggling the polarity and magnitude of an external electric field. Mold polymerization technique: A pre-polymer solution that can be polymerized using free radical polymerization is polymerized in a mold of interest under UV light. The polymer and mold is then placed in contact with an electroactive hydrogel pre-polymer solution (e.g., polyacrylic acid) and the electroactive polymer is polymerized. The polymer construct is removed by allowing it to swell out of the polymer mold in an aqueous solution.
Figure 10A:
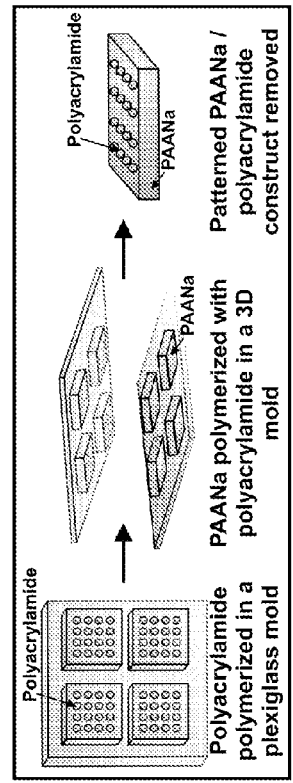
Figure 10A:
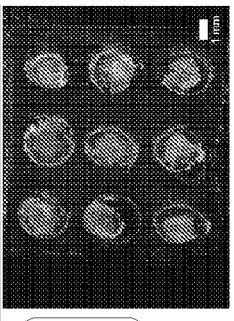
Figure 10B:
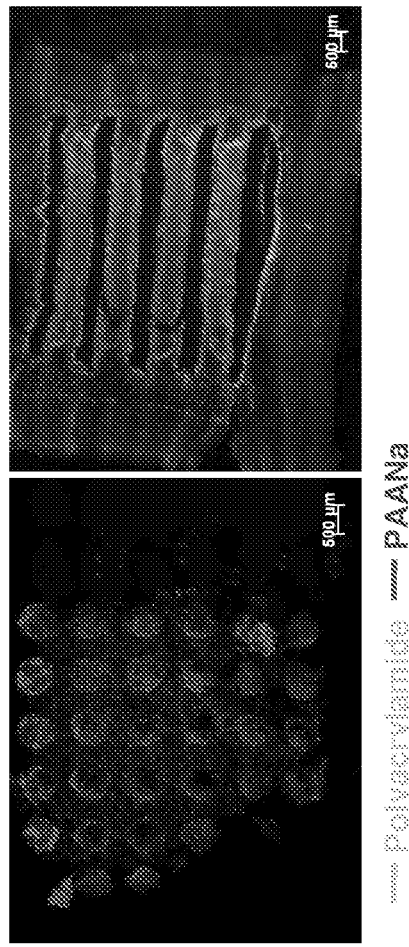

In certain embodiments of the invention, for example as depicted in FIG. 10A, the methods include or further comprise placing a soft polymer polymerization solution in a mold to define features of interest, polymerizing the soft polymer solution and subsequently contacting the polymerized soft polymer with the pre-polymerization emulsion solution in a second mold, which is then polymerized, thereby producing a soft polymer/porous electroactive hydrogel.

A "soft polymer" is any material that is flexible, pliable, or malleable when exposed to an external force. Other physical characteristics common to soft polymers suitable for use in the methods of the invention include linear elasticity and incompressibility. Generally, soft polymers have a Young's modulus in the range of about 1 to about 100,000 pascal (Pa). Non-limiting examples of suitable soft polymers include polyacrylamide gels, poly(N-isopropylacrylamide), pHEMA, collagen, fibrin, gelatin, alginate, and dextran. In preferred embodiments of the invention, the soft polymer is not an electroactive polymer. See, e.g., PCT/US09/45001, the entire contents of which are incorporated herein by reference.

In another aspect of the invention, polymeric fibers, e.g., micron, submicron or nanometer dimension polymeric fibers, are used to create pores within the polymerized hydrogel. As described in U.S. Provisional Patent Application No. 61/177,894, the entire contents of which are incorporated herein by reference, polymeric fibers may be prepared using a rotary spinning system of any suitable material which may be biocompatible or nonbiocompatible and include, for example, poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly (vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyphosphazenes, polygermanes, and polyorthoesters, polyesters, polyamides, polyolefins, polycarbonates, polyaramides, polyimides. The polymers may also be naturally occurring polymers e.g., proteins, polysaccharides, lipids, nucleic acids or combinations thereof. The polymeric fiber may also be made from a degradable polymer, e.g., a polymer that is degraded in an organic solvent, such as acetone, water, or salt water. Examples of such polymers include polystyrene, or a starch based polymer, such as poly(lactide-co-glycolides). Once the fibers are formed, they may be placed in a mold and the pre-polymer solution is poured into the mold. Alternatively, the pre-polymer solution may be placed in the mold prior to the polymeric fibers. In either case, following the placement of the polymeric fibers and the pre-polymer solution into a mold, an oxidizing agent is added to generate an electroactive hydrogel and a disperse water insoluble solution. Subsequently, the polymeric fibers are dissolved generating the pores in the hydrogel, thereby forming the porous electroactive hydrogel.

In various embodiments of the invention, the methods may further include placing the emulsion in a mold and/or placing a photolithographic mask on top of the emulsion to define features of interest. In embodiments when the emulsion is placed in a mold, following polymerization, the porous electroactive hydrogel may be placed in, e.g., a water or a saline solution, causing it to swell out of the mold. For example, a photolithographic mask or patterned transparency with dark and white regions may be used to selectively polymerize regions of interest and to create patterns of interest in the hydrogel or engineer structural gradients in the hydrogel. Polymer molding techniques may also be used to generate the desired polymer patterns. For example, a polymer with repeatable geometries, e.g., a PDMS mold or a polymethyl methacrylate (PMMA) mold may be generated.

Polymer molds are created with a drawing program such as CorelDraw or AutoCAD, and prescribed to a laser cutting tool. The laser cutting tool etches the desired dimensions of the polymer mold into a plexiglass sheet. Two sheets are etched using the laser cutting tool; one for the soft polymer embedded in the electroactive hydrogel and one for the electroactive hydrogel (FIG. 10A). The two molds fit together like puzzle pieces, in order to pattern the two polymer constructs in three dimensions. The soft polymer is first polymerized in the desired mold, and subsequently placed in contact with the electroactive pre-polymer solution. The electroactive hydrogel is polymerized in the second mold. The soft polymer/electroactive hydrogel construct is then exposed to water or a salt solution, such that the molded polymer expands out of the mold due to swelling.

In certain embodiments, the mold may comprise a pattern, for example a pattern comprising grooves of dimensions of about 1 millimeter by about 1 millimeter by about 5 millimeter, about 0.5 millimeter by about 0.5 millimeter by about 2.5 millimeter, about 0.1 millimeter by about 0.1 millimeter by about 0.5 millimeter, about 1.5 millimeter by about 1.5 millimeter by about 5 millimeter, or about 2 millimeter by about 2 millimeter by about 5 millimeter. It should be understood that dimensions intermediate to the above-recited dimensions are also contemplated by the present invention.

The methods of the invention may also further comprise seeding cells on the porous electroactive hydrogel and culturing the cells such that, e.g., a tissue, such as an anisotropic tissue, forms. Any suitable cells may be seeded on the hydrogels described herein. For example, suitable cells include, without limitation, stem cells, embryonic cells, neonatal cells, including muscle cells, skin cells, glandular or endocrine cells, corneal cells, neuronal cells, and/or adipose cells. As used herein, muscle cells include smooth muscle cells, striated muscle cells (skeletal), or cardiac cells. Stem cells including embryonic (primary and cell lines), fetal (primary and cell lines), adult (primary and cell lines) and iPS (induced pluripotent stem cells) may be used. Cells may be normal cells or abnormal cells (e.g., those derived from a diseased tissue, or those that are physically or genetically altered to achieve a abnormal or pathological phenotype or function), normal or diseased cells derived from embryonic stem cells or induced pluripotent stem cells, or normal cells that are seeded/printed in an abnormal or aberrant configuration. Cells from any species can be used so long as they do not cause an adverse immune reaction in the recipient.

To seed cells, hydrogels are placed in culture with a cell suspension allowing the cells to settle and adhere to the hydrogel. The cells on the hydrogel may be cultured in an incubator under physiologic conditions (e.g., at 37° C.). One of ordinary skill in the art may readily determine appropriate seeding concentrations, suitable culture times, and suitable culture media.

In one embodiment, the methods of the invention do not further comprise seeding cells on the porous electroactive hydrogel.

For application of an electrical field to induce movement/actuation of the porous electroactive hydrogel, electrodes are required to apply a voltage in a physiological saline solution without corrosion. Exemplary electrodes include gold, platinum, and titanium platinized anode electrodes. A voltage source is used to apply voltage to the electrodes to actuate the hydrogel.

Figure 2:
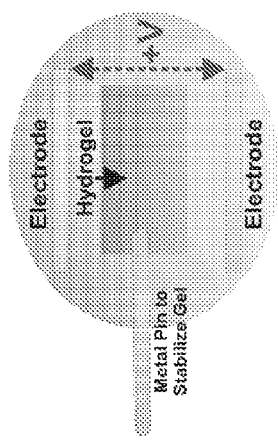
FIG. 2 is a diagram showing a hydrogel placed between two electrodes in a saline solution. Voltages of 1-5 V are applied between the electrodes.

The performance, e.g., electroactuation, of the hydrogel constructs may be determined as described in the appended examples. For example, the hydrogel may be preconditioned in a solution having a desired pH and may optionally be tethered using a small pin or needle. Electrodes are placed alongside the hydrogel in a solution and a voltage of about 1 to about 5 V is applied as needed. In some cases the polarity of the voltage is toggled between 2 electrodes. The resulting deformation of the hydrogel may be imaged under a stereo microscope using a CCD camera. FIG. 2 shows an exemplary setup for evaluating bending/deformation of the hydrogel in response to the application of an electrical field to the hydrogel.

III. Uses of the Porous Electroactive Hydrogels of the Invention

The porous electroactive hydrogels described herein have numerous applications and uses, including, for example, uses as microactuators, in regenerative medicine, tissue engineering, biosensing, biofouling, drug delivery, and drug discovery.

Figure 9:
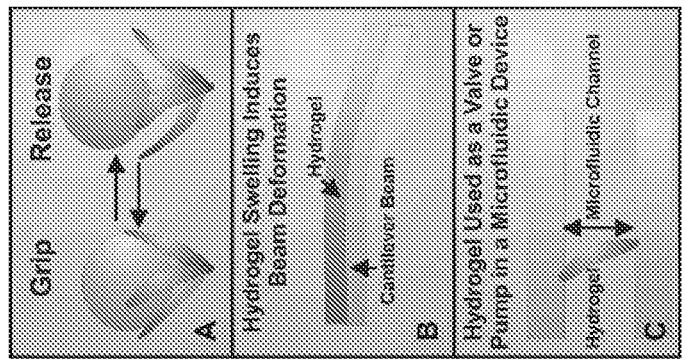
FIGS. 9A-9C are diagrams of soft robotic manipulators and the application of electroactuated hydrogels for grip/release function (A), beam deformation (B), and mediation of fluid passage in a channel (C).

In one embodiment, the porous electroactuated hydrogels can be utilized for a variety of actuation applications in aqueous solutions. For example, the porous electroactuated hydrogels may be used to grip and release objects or pharmaceutically active agents of interest via application of an external electric field (see FIG. 9A). The porous electroactive hydrogels may also be integrated into micro- and macro-scale mechanical components to initiate and control beam bending and actuation (see FIG. 9B). In another embodiment, the porous electroactuated hydrogels may be used as valves or pumps in a microfluidic device. For example, the porous electroactuated hydrogels may be integrated into microfluidic channels of a microfluidic device, such that a change in pH or application of an external electric field can mediate the rate of fluid passing through the channel, thereby simulating the action of a valve or a pump (see FIG. 9C). In another embodiment, the porous electroactuated hydrogels may also be utilized for actuation in robotic applications as soft robotic manipulators without the need for complex electromechanical devices.

Figure 6:
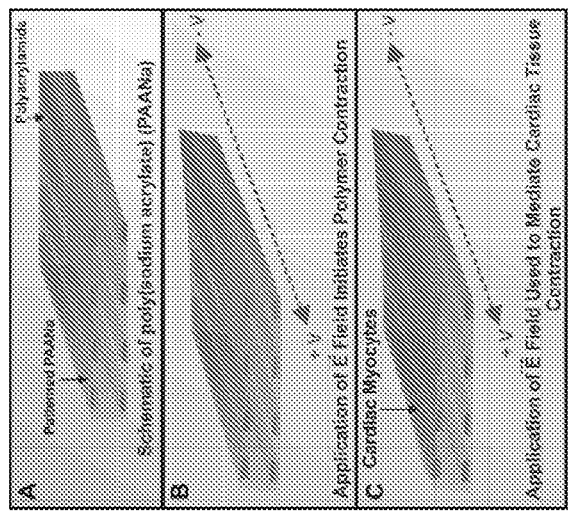
FIGS. 6A-6C are a series of diagrams showing the use of soft polymer substrates to stretch cells and tissues.

In another embodiment, the porous electroactive hydrogels may be used to stretch or alter cells and tissues, e.g., alter cell and tissue architecture, in vitro or in vivo. In this embodiment, a porous electroactive hydrogel is seeded with cells of interest, e.g., cardiomyocytes. The porous electroactive hydrogel may further comprise an extracellular matrix protein to facilitate adherence of the cells to the hydrogel. Once cells are adhered to the hydrogels, a voltage may be applied such that the hydrogels stretch in the desired direction (see FIGS. 6A-C). A change in the magnitude or polarity of the applied voltage deforms the shape of the cell, plurality of cells, or artificial tissues. For example, such porous electroactive hydrogels may be seeded with cardiac myocytes to prepare a biohybrid artificial muscle construct comprised of biological and synthetic muscle (the porous electroactive hydrogel). Moreover, such porous electroactive hydrogels may be used in experimental settings to measure the changes in cell tractional forces when the porous electroactive hydrogel seeded with cells is stretched in the desired direction.

Figure 7:
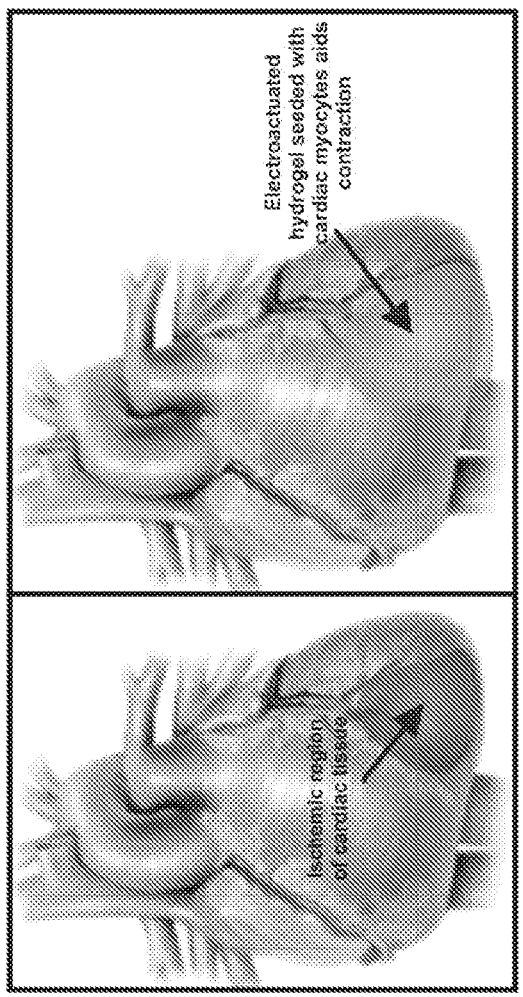
FIG. 7 is a diagram showing the use of electroactive hydrogels as polymer ventricular assist devices. The figure on the left shows a heart with an ischemic region of cardiac tissue, and the figure on the right shows application of an electroactuated hydrogel patch seeded with cardiac myocytes to aid contraction.

The porous electroactive hydrogels of the present invention are also useful for simulating or augmenting tissue function. For example, porous electroactive hydrogels may be fabricated into a polymeric ventricular assist device as depicted in FIG. 7 without requiring complex electromechanical devices. The device, e.g., in the form of a patch, is useful to augment myocardial function. For example, myocardial tissue is contacted with the hydrogel, e.g., a patch comprising the hydrogel is applied to a portion of myocardial tissue, and an electric field is applied to the hydrogel. Current is systematically toggled on and off or the magnitude or polarity of the applied voltage is systematically altered to achieve the desired level of myocardial function/pumping activity. The porous electroactive hydrogel may further comprises an extracellular matrix protein (ECM) and a cardiomyocyte linked to the ECM.

In yet another embodiment, a porous electroactive hydrogel is placed on regions of damaged (ischemic) cardiac tissue to enhance mechanical continuity throughout the syncytium (see FIG. 7). The porous electroactive hydrogel is used to replace or augment standard ventricular assist devices, which require cumbersome wires and battery packs to aid mechanical function. In this case, only a few electrodes are necessary to control porous electroactive hydrogel deformation and to allow the hydrogel to interact with the native myocardium. The hydrogel may be seeded with cardiac myocytes, such that mechanical continuity throughout the tissue is achieved by the use of a biohybrid artificial muscle.

The porous electroactive hydrogels may also be patterned, casted, or molded with non-electroactive polymers (soft polymers). Soft polymer/porous electroactive hydrogels may be used as models to study mechanical stress gradients in non-electroactive and electroactive polymers. For example, such models may be used in material science to test the effect of mechanical and/or electrical stress on various materials. In addition, if cells are seeded on the soft polymer, the hydrogel, or both the soft polymer and the hydrogel, the effect of mechanical and/or electrical stress on the cells themselves may be tested.

The porous electroactive hydrogels of the invention may also be used as components of artificial limbs and other anatomical structures for which control of movement is desired. For example, a biohybrid prosthetic device may include a support structure comprising an articulating joint (e.g., an artificial prosthetic arm or leg or parts thereof) and a porous electroactive hydrogel affixed thereto.

Figure 8:
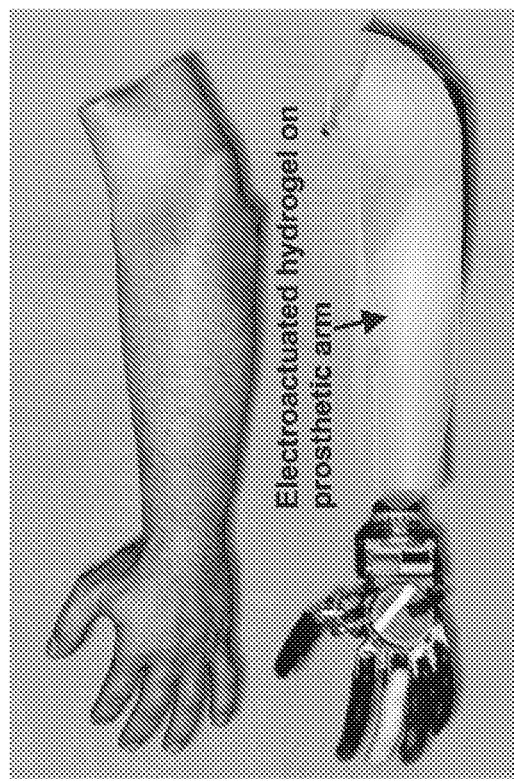
FIG. 8 is a photograph of a biohybrid prosthetic arm and application of an electroactuated hydrogel on the prosthetic arm device.

In one embodiment, a porous electroactive hydrogel is layered on or integrated with prosthetic devices to provide flexibility using a soft polymer that closely resembles native tissue in its mechanical properties (see FIG. 8). Bending and contraction of the hydrogel with the prosthetic device is achieved via the application of an electric field to the prosthetic device, e.g., limb. Muscle tissue is seeded on the porous electroactive hydrogel, such that the hydrogel contracts in the desired direction and interacts with native and seeded tissue. These features substantially improve the biomimetic design of existing prosthetic devices.

In other embodiments, the porous electroactive hydrogels of the invention may be used to inhibit and/or prevent biofouling. For example, any biologically implantable device, e.g., a device implanted for the purposes of muscle stimulation, gastrointestinal stimulation, neural stimulation, or glucose monitoring, such as pacemakers, valves, catheters, stents, defibrillators, neural stimulators, or drug delivery devices may comprise a porous electroactive hydrogel of the invention. The hydrogel may be electroactuated in order to bend and mechanically disrupt any scar and/or fibrotic tissue that may have developed on the device. In certain embodiments, a power supply already present in the implantable device provides a suitable electric field to electroactuate the hydrogel. In embodiments in which the device does not comprise a power supply, a separate power supply may be used to provide a suitable electric field to electroactuate the hydrogel. Such use would significantly reduce the need for explanting of an implanted device on which scar and/or fibrotic tissue has formed.

In another embodiment, the hydrogels may comprise, a pro-apoptotic protein, e.g., a protein that initiates apoptosis or cell death. During deformation of the hydrogel, the pro-apoptotic protein is brought into contact with any scar and/or fibrotic tissue and/or adhesions which may have formed on an implantable device thereby initiating apoptosis or cell death of cells making up the scar and/or fibrotic tissue. In this manner, biofouling of the implantatable device is inhibited.

In other embodiments, the porous electroactive hydrogels may be used to inhibit and/or prevent the growth of microorganisms, e.g., algae and/or bacteria, and/or plankton on a submerged device (e.g., a boat, ship, submarine, wastewater treatment devices, plumbing devices) or medical devices and machines in hospitals, e.g., ventilators. Biofouling of surfaces is common and leads to material degradation, product contamination, mechanical blockage, and impedance of heat transfer in water-processing systems, contamination of drinking water distribution systems, nosocomial infections and blockage of, e.g., catheters and stents. The porous electroactive hydrogels of the present invention may be adhered to any of the above-mentioned devices (e.g., submerged devices or medical devices). Application of an electric field to the hydrogel will cause bending of the hydrogel which will, either mechanically or through the use of a pro-apoptotic protein described above, disrupt the microorganisms attached to the device. In this manner, growth of microorganism on such devices is inhibited.

In another embodiment, the porous electroactive hydrogels of the present invention may be used as real-time chemical and/or pH sensors. For example, hydrogels may be prepared as described herein to include a chromatophore. Any naturally occurring or synthetic chromatophore may be used. Examples of naturally occurring chromatophores include chromatophores that respond to motor nerve stimulation isolated from, e.g., the skin of a cephalopod or fugu fish; or photosynthetic bacteria, e.g., xanthophores, erythrophores, iridophores, leucophores, melanophores, and cyanophores. When the hydrogel flexes due to an electric field and/or pH change, the chromatophore is caused to bend creating a color change which can be detected, e.g., visually detected. Such hydrogels may be used to identify environmental hazards, e.g., pathogens and chemical toxins, such as polynuclear aromatic hydrocarbons, and to monitoring water quality.

As drug carriers, hydrogels may be used in stimuli-responsive drug release devices (for example, using pH or temperature) which may or may not be synchronized with enzymatic or nonenzymatic degradation, e.g., insulin pumps and pain medication pumps.

The porous electroactive hydrogels of the invention may also be used in reservoirs in topical drug delivery, e.g., by iontophoresis, or in dressings for healing of burn or other hard-to-heal wounds.

The porous electroactive hydrogels of the invention may also be used in drug discovery. The moisture content and porosity of the hydrogels mimics animal tissue and the pores within the hydrogel mimic vasculature. As described above, the hydrogels may be used as three-dimensional scaffolds to seed cells, generating an artificial tissue on the microscale level. These hydrogels may be used in, e.g., cell-based drug discovery assays or to analyze the mucoadhesive properties of drugs.

This invention is further illustrated by the following examples which should not be construed as limiting. The contents of all references, patents and published patent applications cited throughout this application, as well as the Figures, are hereby incorporated in reference.

EXAMPLES

In polyelectrolyte hydrogels, such as poly(sodium acrylate) (PAANa), hydrogel contraction in a physiological saline solution depends on the repulsion of $COO^-$ groups within the polymer milieu. The repulsion of $COO^-$ groups is critically dependant on the relative concentration of $COO^-$ moieties relative to COOH and COONa groups. Therefore, within PAANa gels, the diffusion of $Na^+$ ions into the polymer matrix determines the COONa concentration, which determines the entropy of mixing between COO—, COONa and COOH groups. In effect, $Na^+$ diffusion into PAANa gels determines the extent of $COO^-$ repulsion, which determines the magnitude of PAANa swelling (see, e.g., FIGS. 3A-3C).

The degree of $COO^-$ repulsion and hydrogel swelling is modulated by altering the pH of the solution or via application of an electric field, which changes the concentration of COO— groups via the same mechanism. When an electric field is applied across the hydrogel, the spatial extent of Na+ diffusion is mediated throughout the hydrogel, yielding polymer expansion closest to the positively charged electrode due to the excess of $Na^+$ ions present. By toggling the magnitude and polarity of the applied voltage, the spatial extent of $Na^+$ diffusion is controlled and the hydrogel contraction can be dynamically modulated.

Exploiting these principles of hydrogel swelling, a biocompatible, porous electroactive hydrogel with rapid, reversible electroactuation in near neutral pH environments was developed for various applications. An emulsion polymerization technique was used to decrease the $Na^+$ diffusion time in physiological saline solutions, thereby increasing the timescale of porous electroactive hydrogel contraction, as well as the force generated by the porous electroactive hydrogels.

The following materials and methods were used in the Examples below.

Preparation of Poly(Sodium Acrylate) Construct

Initially, a 1% photoinitiator solution of Igracure 2959 (Ciba Specialty Chemicals, Tarrytown, N.Y.) was prepared with 0.225 M maleic anhydride, 5.5 M NaOH, and 2.25 M $Na_2PO_4$ (Sigma-Aldrich, St. Louis, Mo.). All components for the polymerization solution were purchased from Sigma-Aldrich, except Igracure 2959. The solution was mixed and boiled, and subsequently stored at a temperature of 60° C. for 30 minutes. Acrylic acid was added in a 7.3 M concentration and methylbisacrylamide was added in a 0.02 M concentration, after which the polymerization solution was stirred well and stored at 60° C. In some cases, red or green 500 nm diameter polystyrene fluorescent beads (Invitrogen, Carlsbad Calif.) were added in a 1% concentration to enhance imaging of the polymer bending trajectory. Emulsions were prepared using hexane, wherein 30% and 50% volume fractions of hexane/polymerization solution were produced and 0.15 M concentration of Tween 20 surfactant was added to the emulsion solution.

The polymerization solution was added to a plexiglass mold with 0.8 mm×5 mm×1 mm features that was created using a VersaLaser engraving tool (Universal Laser Systems, Scottsdale, Ariz.). A glass slide was placed on top of the emulsion to prevent evaporation of hexane during the polymerization process. The PAANa was polymerized in the plexiglass molds for 15 minutes at a distance of 20 mm from a UV light (XX-15MR Bench Lamp, 302 nm, UVP, Upland, Calif.). Immediately following polymerization, the gels were placed in distilled, deionized (18 Ω/cm) water (Millipore, Billerica, Mass.) at 19° C. The gels swelled out of the molds after 10-15 minutes, at which point the gels were placed in acetone (Sigma-Aldrich, St. Louis, Mo.) for 20-30 minutes to dissolve hexane and unpolymerized monomers present in the gels. The gels were then placed at a temperature of 60° C. to evaporate excess acetone, and subsequently placed in a Normal Tyrode's solution at 19° C., which is commonly used in cell electrophysiology studies. All components for the Normal Tyrode's solution were purchased from Sigma Aldrich (St. Louis, Mo.). The pH of the Normal Tyrode's solution was equilibrated to 7.40 at 37° C. with the addition of NaOH or HCl in order to remain consistent with previous cell and tissue electrophysiology studies. Since the Normal Tyrode's solution contains ~20× higher concentration of NaCl as compared to other electrolytes, the solution was assumed to be a 135 mmol NaCl solution when analyzing the effects of various ions on the hydrogels. The pH of the NT solution was 7.49 at 19° C. after equilibration. The PAANa hydrogels were equilibrated in the Normal Tyrode's solution at 19-23° C. for at least 20 hours prior to an experiment.

Scanning Electron Microscopy (SEM) Imaging

After the water was removed from PAANa during polymerization, the hydrogels were soaked in acetone. The acetone was subsequently evaporated from the gels in 60° C. oven for at least 1 hour. For swelling measurements, the gels were frozen in liquid nitrogen and the water was subsequently removed in a $CO_2$ dryer (Labconco FreeZone 6, Fort Scott, Kans.). The dry hydrogels were coated with Pt/Pd using a sputter coater (Denton Vacuum, Moorestown, N.J.). The gels were then imaged using a Zeiss Ultra 55 scanning electron microscope (Carl Zeiss, Dresden, Germany) with a 5 kV voltage and a 5 mm working distance.

Electroactuation Measurements

After equilibration in the Normal Tyrode's solution, the PAANa gels were placed in a 35 mm tissue culture dish (Corning, Corning, N.Y.) coated in a ~5 mm thick layer of polydimethylsiloxane (Dow Corning, Midland, Mich.). The tissue culture dish was placed in a custom holder, with slots for placement of two 20 mm×25.4 mm×2 mm platinized titanium electrodes (Idea Scientific Company, Minneapolis, Minn.). The electrodes were placed 20 mm apart and connected to a DC power source (RSR Electronics, Avenel, N.J.). The PAANa gels were fixed at one end to the underlying polydimethylsiloxane substrate using a 0.2 mm diameter stainless steel minutien pin (Fine Science Tools, Foster City, Calif.). After the PAANa gel was affixed appropriately, 4 mL of Normal Tyrode's solution was added at a 19-23° C. temperature and 3 or 5 V were applied between the electrodes for 3 minutes. Imaging was performed on a Leica MZ12.5 stereomicroscope (Leica, Wetzlar, Germany) using a Basler camera (Highland, Ill.). Images were collected at a frame rate of 1 frame/sec using a custom LabView (National Instruments, Austin, Tex.) imaging collection program. Fluorescence imaging of the PAANa bending trajectory was performed on a Zeiss M2 Bio stereomicroscope (Carl Zeiss, Dresden, Germany) using a Zeiss AxioCam MRM camera at a frame rate of 1 frame/sec. Filter sets for GFP 470 and rhodamine were employed to collect fluorescence images.

As shown in FIG. 4d, the X-Y position of the hydrogel end was calculated after application of 1.5 V/cm or 2.5 V/cm electric fields for 3 minutes. The bending angle was normalized to the initial bending angle at time 0, which was typically 0+5 degrees. Imaging analysis of PAANa bending angle trajectories was performed by creating binary images of fluorescent hydrogels, filtering and skeletonizing the images, and subsequently calculating the change in angle at each timepoint. Image analyses were performed in MATLAB (MathWorks, Natick, Mass.). A two-sample t-test ($p<0.01$) was used to determined statistical significance between data points.

Measurements of PAANa Deswelling

To quantify the extent of polymer deswelling, PAANa gels polymerized in 5 mm×5 mm×1 mm molds were placed in a 7.5 pH solution with 0.1 M $Na_2PO_4$ and 0.1 HEPES (Sigma-Aldrich, St. Louis, Mo.) pH buffers for 24 hours. The gels were then placed in HEPES and $Na_2PO_4$ buffered pH solutions of 3.0 and 12.0. The mass of the gels after equilibration in a pH 7.5 solution was compared to the mass of the gels after 24 hours in pH 3.0 and pH 12.0 solutions, and the % deswelling (D) was calculated as:

$$D = \left| \frac{W_{pH\_3,12} - W_{pH\_7.5}}{W_{pH\_7.5}} \right| \times 100$$

where $W_{pH\_7.5}$ represents the gel weight after equilibration in a pH 7.5 solution, and $W_{pH\_3,12}$ represents the gel weight in pH 3.0 and 12.0 solutions.

Elasticity Measurements

An AR-G2 rheometer (TA Instruments, New Castle, Del.) applied uniaxial compression to the PAANa gels to determine their mechanical properties. Parallel plates applied compression to cylindrical gels with diameter approximately 20 mm. Maximum strain reached 10% applied at 50 µm/sec. The PAANa gels were assumed to be linearly elastic. The elastic modulus was found with a least squares linear fit of the stress-strain curves.

Imaging of pH Gradients

Imaging of pH gradients was performed using the Leica stereomicroscope setup described above, utilizing a Nikon Coolpix 4500 digital camera (Nikon, Tokyo, Japan) to capture images every 30 seconds for 3 minutes. When conducting experiments, 0.02% phenol red (Sigma Aldrich, St. Louis, Mo.) was added to the Normal Tyrode's. Phenol red is a pH indicator for pH values of 6.6-8.2, where a bright yellow color indicates a pH of pH 6.6 or lower and a bright magenta color indicates a pH of 8.2 or above. Once the experimental setup was arranged, the lighting, magnification, focus and placement of electrodes remained unchanged throughout the experiment. Calibration images of 0.1 M HEPES, 0.1 M Tris and 0.05 M $Na_2PO_4$ (Sigma Aldrich, St. Louis, Mo.) pH buffers in deionized water at pH values of 6.5, 7.0, 7.5, 8.0 and 8.5 were collected with 0.02% phenol red present in solution.

Analysis of Hydrogel Stretch Ratio

Imaging analysis of PAANa bending angle trajectories was performed by creating binary images of fluorescent hydrogels, automatically finding the perimeter of the gels, and subsequently calculating the change in length of the top and bottom of the gel at each time point. The polymer length at the top and bottom of the gel at each time point was compared to the initial length of the gel, and a shortening ratio was calculated. Image analyses were performed in MATLAB (Math-Works, Natick, Mass.).

Measurements of PAANa Swelling

To quantify the extent of polymer swelling, dry PAANa gels were weighed and the dimensions measured by imaging with a Zeiss M2 Bio stereomicroscope (Carl Zeiss, Dresden, Germany) using a Zeiss AxioCam. Thickness of the gels was measured using digital calipers. The gels were then placed in 0.1 M HEPES and $Na_2PO_4$ buffered pH solutions of 3.0, 7.5 and 12.0. The mass of the gels after 24 hours was then quantified, as well as the dimensions and thickness of the gels after hydration.

Force Measurements

Force measurements of PAANa bending were conducted using the same setup as the electroactuation measurements. One end of the PAANa gel was affixed to an underlying polydimethylsiloxane substrate and the other end was tethered to a force gauge which recorded the force generated during polymer bending. Imaging was performed on a Leica MZ12.5 stereomicroscope (Leica, Wetzlar, Germany) using a Basler camera (Highland, Ill.). A two-sample t-test (p<0.01) was used to determined statistical significance between data points.

Example 1

Preparation and Actuation of Porous Electroactive Hydrogels

Figure 4:
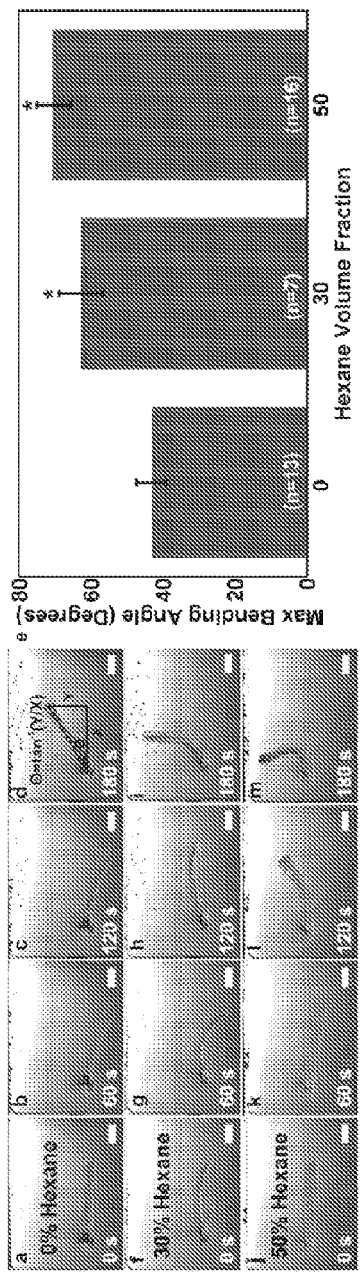
FIGS. 4A-D and F-M are a series of photographs showing the response of hydrogels to application of an electrical field. Hydrogels with varying hexane volume fractions in a Normal Tyrode's solution after 0 min (a,f,j), 1 min (b,g,k), 2 min (c,h,l) and 3 min (d,i,m). The bending angle (θ) of the hydrogel is calculated by determining the position of the end of the hydrogel on the x-y coordinate (d).
FIG. 4E is a graph showing the maximum bending angle of the hydrogels versus hexane volume fraction demonstrating that more porous hydrogels bend to a larger degree. Error bars represent the standard error of the mean (s.e.m.) of the measurements. Scale bar=2 mm.

In order to optimize the electroactive hydrogel bending, an emulsion templating technique was employed to increase the hydrogel porosity (FIG. 1). The size of pores primarily depended on the volume fraction of the oil phase (hexane) utilized and the concentration of surfactant (Tween 20) added. Employing the emulsion templating method, a polydisperse distribution of pore sizes was generated, with the diameter of the smallest pores being ~10 µm (FIG. 1c, d). By creating porous hydrogels using emulsion templating, bending angles of 70-90° were achieved with 2.5 V/cm electric field applied for 3 minutes (FIG. 4). This result represents a substantial improvement over previous studies where maximum bending angles of −30° to −40° (towards the cathode) were achieved when the electroactive hydrogels with the same dimensions were placed in 1.5 V/cm electric fields for 2 minutes (Moschou, E. A. et al. (2004) Chem. Mater. 16, 2499-2502; Moschou, E. A. et al. (2006) Sensor Actuat. B-Chemical 115, 379-383).

Figure 13:
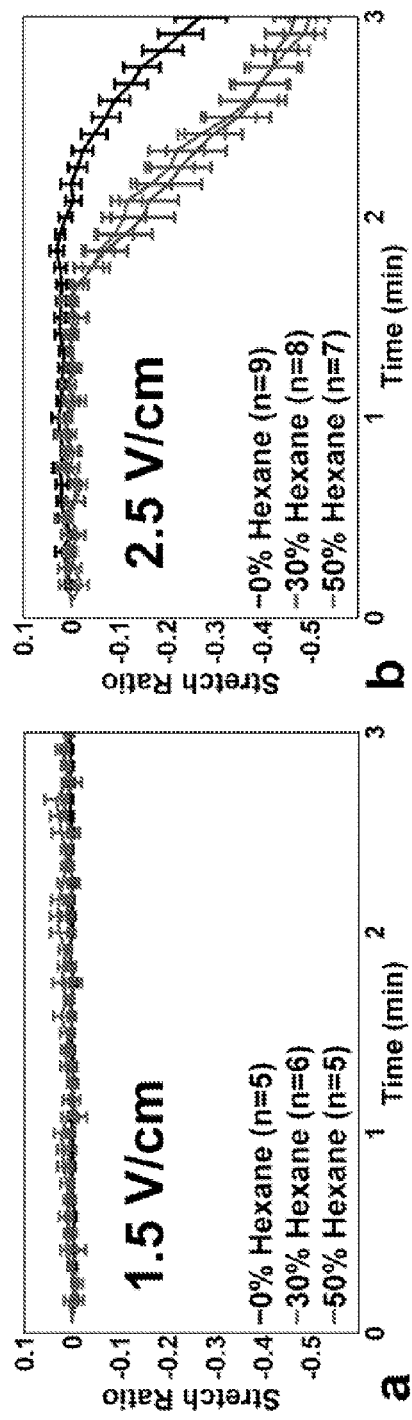
FIGS. 13A-13B are graphs showing the stretch ratio of the hydrogel as a function of time when 1.5 V/cm (a) and 2.5 V/cm (b) are applied. When 2.5 V/cm is applied to the hydrogel in the saline solution, the hydrogel begins to shorten after 120 s, once a significant pH gradient has been established. After 180 s with 2.5 V/cm applied, non-porous hydrogels produced a maximum stretch ratio (shortening) of −0.349±0.066 (n=9, s.e.m) after 180 s, but PAANa gels polymerized in a 30% hexane yielded a maximum stretch ratio of −0.508±0.032 (n=8, s.e.m) and PAANa gels polymerized in a 50% hexane emulsion produced a maximum stretch ratio of −0.508±0.047 (n=7, s.e.m.)

The results indicated that for PAANa gels polymerized without an emulsion, bending angles of 43.2°±14.8° (towards the anode) were achieved (n=13, s.d.). However, PAANa gels polymerized in a 30% hexane emulsion produced average bending angles of 62.8°±16.2° (n=7, s.d.) and PAANa gels polymerized in a 50% hexane emulsion generated bending angles of 70.4°±20.0° (n=16, s.d.). Employing a 2-sample student's t-test, the maximum bending angle of the PAANa gels polymerized in 30% and 50% hexane were found to be statistically significant from the non-porous PAANa (p<0.01). The PAANa gels polymerized with 30% and 50% hexane may be statistically insignificant because >30% of a disperse phase in an emulsion generally represents when close packing of the disperse phase occurs (Mason, T. G., et al. (1995) Phys. Rev. Lett. 75, 2051-2054), such that close-packing of hexane droplets may have occurred for >30% volume fractions in the emulsion. In addition, non-porous hydrogels shortened 34.9±6.6% (n=9, s.e.m) after 180 s, but PAANa gels polymerized in a 30% hexane shortened 50.8±3.2% (n=8, s.e.m) and PAANa gels polymerized in a 50% hexane emulsion shortened 50.8±4.7% (n=7, s.e.m.), highlighting the enhanced flexibility of the porous hydrogels (FIG. 13). Overall, these results demonstrate that electroactuation of PAANa gels can be improved by >60% when an emulsion templating technique is utilized. Moreover, bending angles of more than 90° are difficult to achieve, since these large bending angles require an ionic and pH gradient to buildup across the hydrogel while the gel is parallel to the electric field. Therefore, the bending angles of 70-90° achieved here represent an optimized actuation of PAANa hydrogels.

Figure 5:
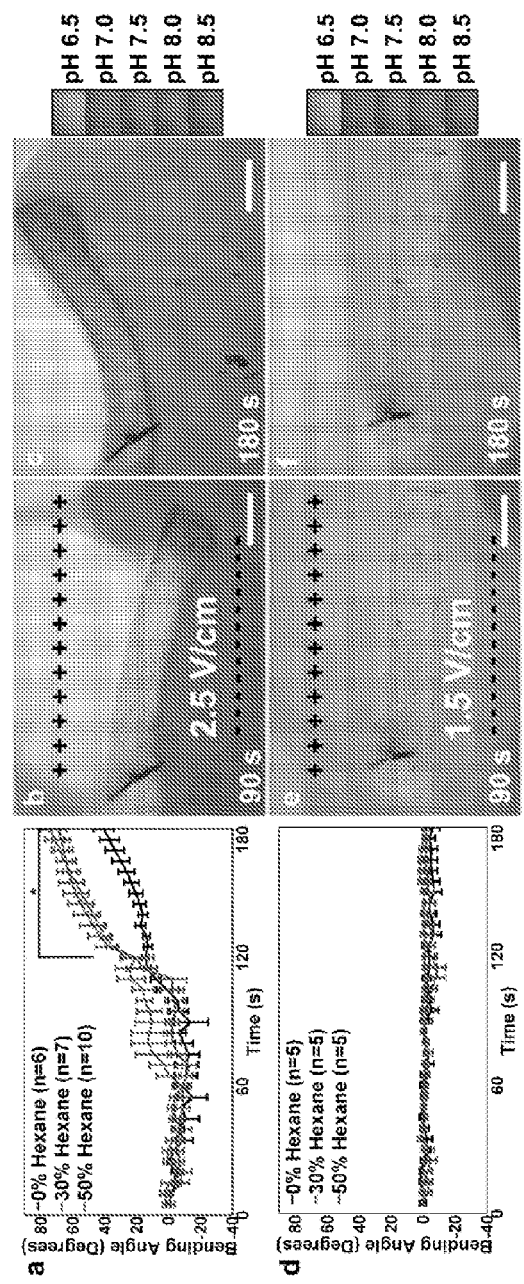

Interestingly, despite the increased actuation of porous PAANa hydrogels, during the first 60-100 s after an electric field was applied, the trajectory of the PAANa gels was strikingly similar to the non-porous hydrogels (FIG. 5), and almost no deformation was generated in the hydrogel (FIG. 13). As shown in FIG. 5, when 2.5 V/cm was applied for 3 minutes, the porous hydrogels only bent to a greater extent than the non-porous hydrogels after an electric field was applied for 120-130 seconds. Employing a 2-sample t-test, the bending angle of the PAANa gels polymerized in 30% and 50% hexane were found to be statistically significant from the non-porous PAANa gels (p<0.01) after 125 seconds. Furthermore, the hydrogels first bent towards the cathode, and then began to bend toward the anode after ~100 s, wherein large bending angles were achieved. Finally, when only 1.5 V/cm was applied (FIG. 5D-5F), bending of the porous hydrogels was not discriminable from the non-porous hydrogels, and the gels slowly inched towards the cathode instead of the anode. Overall, the pH gradient surrounding the hydrogel and the polymer bending trajectory demonstrate that the spatiotemporal pH gradient across the PAANa hydrogel is critically important in achieving large bending angles. These results indicate that a large pH gradient is required to generate large hydrogel bending, primarily due to formation of COOH groups on the anode side of the gel.

Example 2

Effects of a Spatiotemporal pH Gradient on Porous Electroactive Hydrogel Bending In this experiment, the effect of the spatiotemporal pH gradient on hydrogel bending, as well as the mechanisms underlying large bending of porous PAANa hydrogels were determined. The timescale and magnitude of these pH gradients can explain why larger deformation of PAANa hydrogels occurs in stronger electric fields. As larger electric fields are applied, a steeper pH gradient was created across the hydrogel (FIG. 5$b,c$), thus yielding a spatial gradient of COOH and COO$^-$ groups within the hydrogel. As more COOH groups were created within the hydrogel on the anode side relative to the cathode side, the polymer compressed on the COOH dominant (anode) side, generating a large bending angle.

Figure 3:
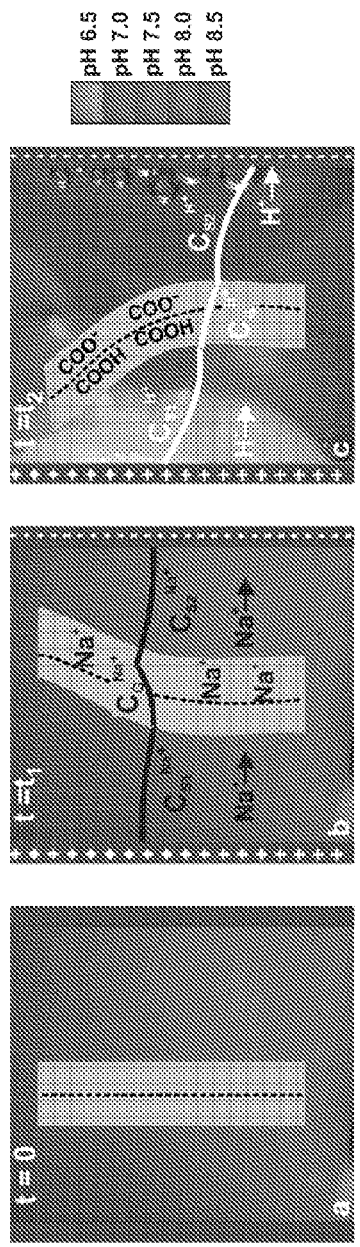
FIGS. 3A-3C are diagrams schematically showing the process of hydrogel swelling as the result of ionic distributions in the hydrogel and the surrounding physiological saline solution before (a) and after (b,c) an electric field is applied. The CG, CS1 and CS2 concentrations indicated the H+ and Na+ concentrations in the gel, the anode side of the solution, and the cathode side of the solution, respectively. When no electric field is applied, the gel is in equilibrium with the surrounding solution. Once an electric field is applied, the CGNa+ concentration on the cathode side of the gel increases, causing the gel to bend towards the cathode (b). Once a pH gradient is created across the gel, the COOH concentration at the anode side of the gel increases, causing the gel to bend towards the anode (c).

The process of PAANa hydrogel bending is illustrated schematically in FIG. 3, where the extent of ionic gradients in the gel ($C_G^{Na+}$, $C_G^{+}$) depend on the fixed concentration of negative charges in the gel. Before an electric field was applied, the gel was in equilibrium with the surrounding solution (FIG. 3$a$). Once an electric field was applied, movement of cations (Na$^+$) influenced the bending of the hydrogel (Moschou, E. A., et al. (2004) *Chem. Mater.* 16, 2499-2502; Moschou, E. A. et al. (2006) *Sensor Actuat. B-Chemical* 115, 379-383; Shiga, T. (1997) *Adv. Polym. Sci.* 134, 131-163; Yao, L. and Krause, S. (2003) *Macromolecules* 36, 2055-2065; Wallmersperger, T., et al. (2004) *Mech. Mater.* 36, 411-420; Yew, Y. K., et al. (2007) *Biomed. Microdevices* 9, 487-499). As shown in FIG. 3$b$, once an electric field was applied, the concentration of Na$^+$ ions on the anode side of the gel ($C_{G1}^{Na+}$) increases while the concentration of Na$^+$ ions in solution on the anode side of the gel ($C_{G1}^{Na+}$) decreases. This produces an increase in osmotic pressure on the anode side of the gel occurs, causing this side of the gel to swell. Conversely, $C_{G2}^{Na+}$ and $C_{S2}^{Na+}$ increase on the cathode side of the gel, which may lead to some gel de-swelling. Anions (Cl$^-$) did not have as much of an effect on the hydrogel bending, since the diffusion of Cl$^-$ in water is much lower than that of Na$^+$. Previous studies have shown that Na$^+$ diffuses 28% faster in water at 25° C. (Koneshan, S., et al. (1998) *Phys. Chem. B* 102, 4193-4204). Consequently the concentration of Na$^+$ ions on the anode side of the gel increased (FIG. 3$b$), which increased the osmotic pressure on the anode side of the gel and caused the gel to bend towards the cathode (Moschou, E. A., et al. (2004) *Chem. Mater.* 16, 2499-2502; Moschou, E. A. et al. (2006) *Sensor Actuat. B-Chemical* 115, 379-383; Shiga, T. (1997) *Adv. Polym. Sci.* 134, 131-163; Yao, L. and Krause, S. (2003) *Macromolecules* 36, 2055-2065; Mason, T. G., et al. (1995) *Phys. Rev. Lett.* 75, 2051-2054).

However, oxidation at the anode generated H$^+$ ions, which decreased the pH at the anode (Doi, M., et al. (1992) *Macromolecules* 25, 5504-5511; Yew, Y. K., et al. (2007) *Biomed. Microdevices* 9, 487-499). Conversely, reduction of the saline solution depleted the H$^+$ concentration to form a hydrogen gas, which increased the pH at the cathode. Since the H$^+$ concentration on the anode side of the gel ($C_{S1}^{H+}$) was greater than the cathode side of the gel ($C_{S2}^{H+}$), the relative concentration of COOH at the anode side of the gel was much higher than that on the cathode side of the gel (Shiga, T. (1997) *Adv. Polym. Sci.* 134, 131-163; Doi, M., et al. (1992) *Macromolecules* 25, 5504-5511; Wallmersperger, T., et al. (2004) *Mech. Mater.* 36, 411-420). Hence, the cathode side of the gel had a large concentration of COO$^-$ ions relative to COOH groups, such that the anode side of the gel compressed significantly due to a higher concentration of COOH groups that do not repulse one another as strongly (FIG. 3$c$). Therefore, the bending of the gel towards the cathode and then the anode was due to the COOH gradients generated across the hydrogel. In essence, the deswelling of the anode side of the PAANa hydrogel produced large deformation.

Example 3

Effects of Porous Electroactive Hydrogel Density and Elasticity on Bending

Figure 11:
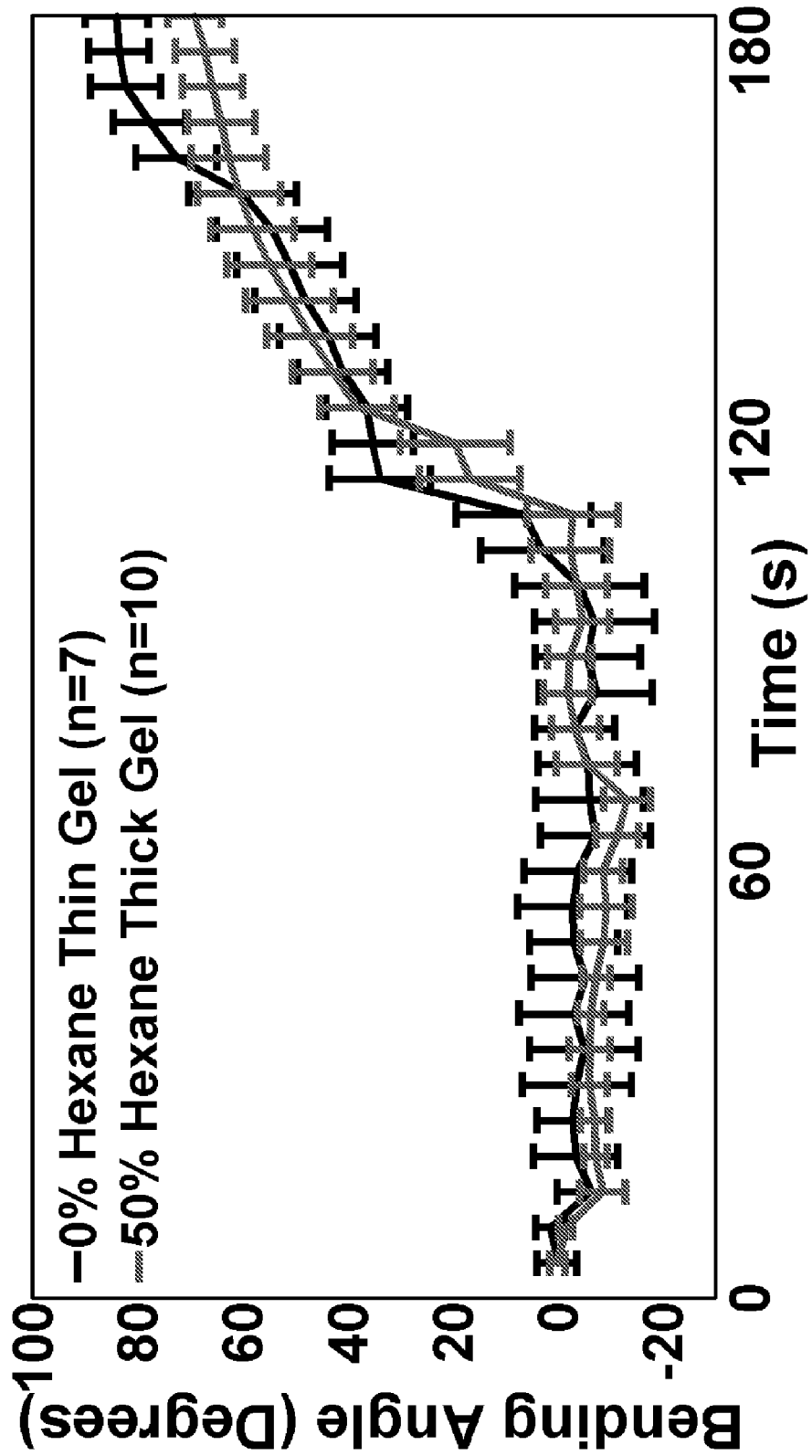
FIG. 11 is a graph showing that when the non-porous gels were engineered to be 50% thinner (~1 mm thick, black line), these gels followed the same trajectory as the ~2 mm thick porous hydrogels produced using a 50% emulsion. This result indicates that the cross-sectional area and volume density of the PAANa gel has a significant influence of polymer contraction, since these parameters determine the concentration of COOH and COO— groups across the gel slab.

Overall, both porous and non-porous hydrogels bend in a similar manner due to ion diffusion when no strong pH gradient is present. However, once a pH gradient is present, porous hydrogels produce larger bending angles than non-porous hydrogels since porous gels are less dense, such that they require less deswelling and compression on the anode side of the gel to produce a bending motion. For instance, a porous gel will have more void space and less polymer material within the cross-sectional area of the gel. Since the porous gels have less polymer material within the cross-sectional area of the gel, a smaller concentration of COOH groups must be generated across the cross-sectional area of the gel to cause the porous polymer to compress. It was observed that 50% thinner, non-porous hydrogels follow the same bending trajectory as porous hydrogels. Thin, non-porous hydrogels are able to bend to the same extent as porous hydrogels because the concentration of COOH groups necessary to cause polymer contraction at the anode side of a thin gel is smaller relative to thicker gels (FIG. 11). Furthermore, the mass per unit volume of the porous and non-porous hydrogels was found to be equivalent (FIG. 14), indicating the comparable bending of thin, non-porous hydrogels and thick porous hydrogels cannot be attributed to differences in water content. Therefore, the bending rate is critically dependent on PAANa density and cross-sectional area, since the cross-sectional area determines the relative concentration of COOH and COO$^-$ groups across the gel.

Example 4

Effects of Deswelling on Porous Electroactive Hydrogel Bending

Figure 12:
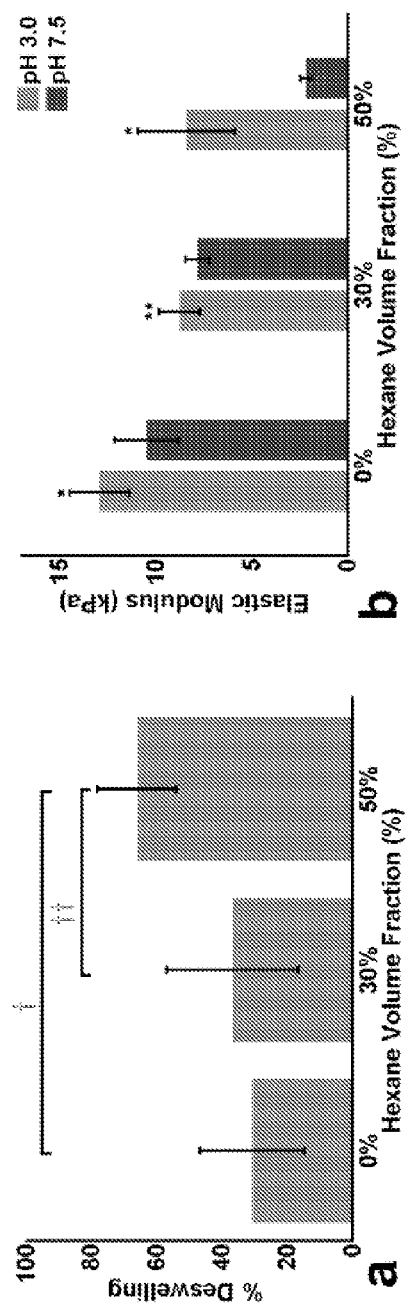
FIGS. 12A-12B are graphs showing that after equilibration in a heavily buffered pH 7.5 solution and placement in a pH 3.0 solution, PAANa hydrogels produced in a 50% emulsion deswell nearly two times more than non-porous hydrogels and PAANa hydrogels produced in a 30% emulsion (a). Moreover, porous hydrogels produced in a 50% emulsion increase in stiffness nearly 295% when exposed to a pH 3.0 solution, as compared to an 18% increase in stiffness for non-porous hydrogels. A student's 2-sample t-test was utilized to test for statistical significance, where † corresponds to $p > 0.001$, †† indicates $p > 0.001$, * indicates $p > 0.01$ and ** indicates $p > 0.05$.
Figure 16:
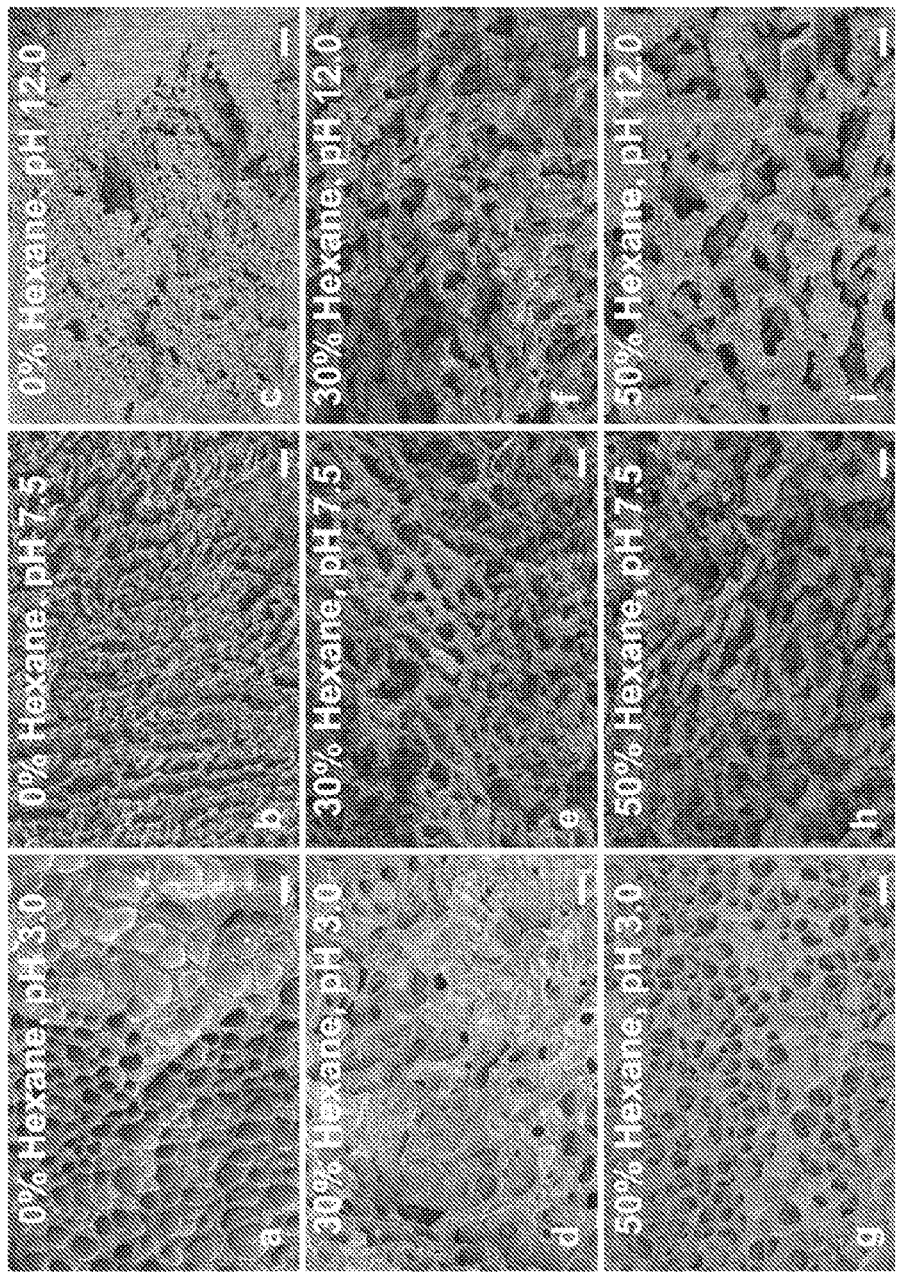
FIGS. 16A-16I are SEM images of porous and non-porous PAANa gels after prolonged exposure to pH 3.0 (a,d,g), pH 7.5 (b,e,h), and pH 12.0 (c,f,i) solutions. In porous hydrogels, more void was present at pH 7.5 (e,h) and pH 12.0 (f,i) as compared to the non-porous hydrogels (b,c). Upon deswelling, the non-porous hydrogels formed a solid structure (a) that did not drastically decrease the amount of void space present as compared to the non-porous hydrogels in pH 7.5 (b). Conversely, drastic reductions in the void space present in porous hydrogels were observed at pH 3.0 (d,g) as compared to pH 7.5 (e,h). These results further show that porous PAANa hydrogels have enhanced deswelling properties in the presence of low pH solutions. Scale bar=10 μm.

The density and cross-sectional area of the PAANa gels also influence their deswelling properties, since porous hydrogels have a large percentage of void space compared to dry hydrogels. The PAANa gels contract when an electric field is applied as a result of formation of COOH groups on the anode side of the gels, leading to shrinkage of the anode side of the gel. Therefore, the contribution of the PAANa deswelling properties to actuation must be considered. After equilibration in a heavily buffered pH 7.5 solution and placement in a pH 3.0 solution, porous hydrogels created in a 50% emulsion deswelled two times more than non-porous hydrogels (FIG. 12a). In particular, porous hydrogels generated in a 50% emulsion deswelled 66±12% (n=8, s.d.), while porous hydrogels generated in a 30% emulsion deswelled 36±30% (n=8, s.d.) and non-porous hydrogels deswelled 30±16% (n=8, s.d.). In effect, these results indicate that porous hydrogels have enhanced actuation properties because they are able to deswell and contract to a larger extent in the presence of low pH solutions. Investigation of the microscale structure of the gels further corroborated the enhanced deswelling properties of porous hydrogels (FIG. 16). When exposed to low pH solutions, porous hydrogels were able to more easily compress as compared to non-porous hydrogels and reduce void spaces initially present in the gels at pH 7.5. These results further suggest that porous PAANa hydrogels have enhanced deswelling properties in the presence of low pH solutions.

Example 5

Elasticity and Force Generation of Porous Electroactive Hydrogels

Utilizing a macroscopic compression test, it was found that porous hydrogels were less stiff and underwent concomitantly larger increases in stiffness when exposed to low pH solutions (FIG. 12b). For instance, when placed in a pH 7.5 solution, the non-porous hydrogels had an elastic modulus of 10.5±1.7 kPa, as compared to the PAANa gels polymerized in a 30% and 50% emulsion which had an elastic modulus of 7.8±0.6 kPa and 2.15±0.2 kPa, respectively. Yet, when placed a pH 3.0 solution, non-porous hydrogels increased in stiffness by 18%, while PAANa gels polymerized in a 50% emulsion increased in stiffness by 295%. This results indicates that the enhanced deswelling of porous hydrogels allows them to stiffen to a larger extent than non-porous hydrogels, thereby improving their actuation when exposed to a strong pH gradient.

In addition, the force generated by the non-porous hydrogels was found to be greater than the porous hydrogels (FIG. 15), owing to the increased stiffness of the non-porous hydrogels. After 180 s with 2.5 V/cm applied, the maximum force generated by non-porous hydrogels was 0.74+0.33 mN (s.d., n=8), as compared to 0.37+0.12 mN (s.d., n=8) for gels created in a 30% emulsion and 0.12+0.06 mN (s.d., n=8) for gels created in a 50% emulsion. However, the force generated could not be normalized by the elastic modulus of the gels, since the elastic modulus dynamically changed as the gels were exposed to strong pH gradients. In essence, the increased elasticity and flexibility of the porous hydrogels contributed to enhanced actuation of these gels, since they were able to bend more easily and to a larger extent.

Overall, the results demonstrate that creating porous hydrogels to enhance ion diffusion throughout the polymer milieu cannot entirely account for large deformation of these gels. Instead, the porosity decreases the cross-sectional area of the gel, such that the gel requires less COOH groups on the anode side of the gel to produce a bending motion. In addition, the porosity decreases the Young's modulus of the PAANa gels and enhances the deswelling and mechanical properties to further improve the actuation of these hydrogels.

In summary, it has been shown that fast hydrogel contraction and large bending angles for poly(sodium acrylate) and other electroactuated hydrogels can be achieved using an emulsion templating method. Fast actuation and large deformation of biocompatible, low voltage polymers is achieved by generating a pH gradient across the polymer, thus altering the entropy of mixing between $COO^-$ and COOH groups. Therefore, porous hydrogels are favorable for electroactuation not only because of they permit faster diffusion of ions, but largely because the cross-sectional area of the gels is smaller such that a smaller pH gradient is required across the hydrogel to initiate bending. In effect, large deformation of hydrogels and fast actuation is due to generation of a pH gradient across the hydrogel surface and enhanced deswelling of the polymer, while slower actuation is due to ion diffusion.

The results demonstrate that in creating fast PAANa actuators with large bending angles, spatiotemporal control of the pH gradient across the hydrogel is critical. By quantitatively measuring the spatiotemporal pH gradient and polymer bending response, it has been shown that the pH gradient has a significantly larger and faster effect on hydrogel bending. Moreover, porous hydrogels bend to a larger extent due to their increased flexibility, decreased volume density, and enhanced deswelling mechanisms. Therefore, porous PAANa hydrogels represent a biocompatible, flexible polymer with fast, reversible electroactuation in near neutral pH environments that can be utilized in soft robotic applications to dynamically mechanical environments in real time. Analysis of the mechanisms underlying large bending of electroactuated hydrogels can be utilized to realize unique applications of these soft robotic systems.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A porous electroactive hydrogel, said hydrogel comprising a polyelectrolyte hydrogel monomer comprising an acrylate group, and a polydisperse distribution of pores throughout the hydrogel, wherein said pores have a radius of about 0.5 micrometers to about 10 micrometers, and wherein said hydrogel bends at an angle of greater than about 45 degrees in the presence of an electric field as compared to the bending of the hydrogel in the absence of said electric field, wherein said pores in said hydrogel are prepared by free radical polymerization of the polyelectrolyte monomer in an emulsion.

2. The hydrogel of claim 1, wherein said electric field comprises about 1-5 volts/cm.

3. The hydrogel of claim 1, wherein said electric field is applied to the hydrogel for about 2 to about 6 minutes.

4. The hydrogel of claim 1, wherein said electric field is applied to the hydrogel for about 3 minutes.

5. The hydrogel of claim 1, wherein said hydrogel comprises an anisotropic pattern.

6. The hydrogel of claim 1, further comprising an electrode.

7. The hydrogel of claim 1, further comprising a voltage source.

8. The hydrogel of claim 1, further comprising a pharmaceutically active compound.

9. The hydrogel of claim 1, further comprising a chromatophore.

10. The hydrogel of claim 1, wherein said hydrogel comprises cells.

11. The hydrogel of claim 10, wherein said hydrogel comprises myocytes.

12. The hydrogel of claim 11, wherein said myocytes are cardiac myocytes.

13. The hydrogel of claim 11, wherein said myocytes are skeletal myocytes.

14. A method for preparing the porous electroactive hydrogel of claim 1, the method comprising contacting a pre-polymer solution of the polyelectrolyte hydrogel monomer comprising an acrylate group with a water insoluble solution and a surfactant, thereby generating a polymer emulsion, wherein the polymer emulsion comprises about 40-80% by volume of the pre-polymer solution and about 20-60% by volume of the water insoluble solution;

contacting the polymer emulsion with an oxidizing agent, thereby generating a porous electroactive hydrogel and a disperse water insoluble solution; and removing the disperse water insoluble solution, thereby preparing a porous electroactive hydrogel.

15. The method of claim 14, further comprising placing a photolithographic mask on top of the polymer emulsion.

16. The method of claim 14, further comprising placing the polymer emulsion in a mold.

17. The method of claim 16, wherein the mold comprises a pattern.

18. The method of claim 17, wherein the pattern comprises grooves of dimensions of about 1 millimeter by about 1 millimeter by about 5 millimeter.

19. The method of claim 14, further comprising seeding cells on the porous electroactive hydrogel and culturing the cells.

20. The method of claim 14, further comprising adding a chromatophore to the hydrogel.

21. The method of claim 14, further comprising adding a protein to the hydrogel.

22. The method of claim 21, wherein the protein is a pro-apoptotic protein.

23. The method of claim 14, further comprising seeding said hydrogel with a cell.

24. The method of claim 23, wherein said cell is selected from the group consisting of a skeletal muscle cell, a smooth muscle cell, and a cardiac muscle cell.

25. A porous electroactive hydrogel prepared according to the method of claim 14.

26. The hydrogel of claim 1, wherein said angle is greater than about 90 degrees.

27. The hydrogel of claim 1, wherein the polyelectrolyte hydrogel monomer comprising an acrylate group is selected from the group consisting of poly(sodium acrylate), poly(ethylene glycol) diacrylate, acrylic acid, polyacrylamide.acrylic acid, hydroxyethyl methacrylate, and derivatives thereof.

* * * * *